United States Patent
Komiyama

(10) Patent No.: US 8,916,714 B2
(45) Date of Patent: *Dec. 23, 2014

(54) METHOD FOR PRODUCING PHENYL-SUBSTITUTED HETEROCYCLIC DERIVATIVE BY MEANS OF COUPLING METHOD USING PALLADIUM COMPOUND

(75) Inventor: Masato Komiyama, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 63 days.

This patent is subject to a terminal disclaimer.

(21) Appl. No.: 13/818,538

(22) PCT Filed: Aug. 26, 2011

(86) PCT No.: PCT/JP2011/069250
§ 371 (c)(1),
(2), (4) Date: Feb. 22, 2013

(87) PCT Pub. No.: WO2012/026565
PCT Pub. Date: Mar. 1, 2012

(65) Prior Publication Data
US 2013/0158272 A1   Jun. 20, 2013

(30) Foreign Application Priority Data
Aug. 27, 2010   (JP) .................................. 2010-190760

(51) Int. Cl.
C07D 277/20   (2006.01)
C07D 417/04   (2006.01)
C07D 277/56   (2006.01)
B01J 31/26   (2006.01)

(52) U.S. Cl.
CPC ............ *C07D 417/04* (2013.01); *C07D 277/20* (2013.01); *C07D 277/56* (2013.01); *B01J 31/26* (2013.01)
USPC ...................................................... 548/201

(58) Field of Classification Search
None
See application file for complete search history.

(56) References Cited

U.S. PATENT DOCUMENTS 8,067,446 B2 * 11/2011 Kawakami et al. ........... 514/354

FOREIGN PATENT DOCUMENTS

| JP | 5785379 | 5/1982 |
| JP | 5995272 | 6/1984 |
| JP | 665210 | 3/1994 |
| JP | 6211815 | 8/1994 |
| JP | 6293746 | 10/1994 |
| JP | 6329647 | 11/1994 |
| JP | 6345724 | 12/1994 |
| JP | 10139770 | 5/1998 |
| JP | 10310578 | 11/1998 |
| JP | 11060552 | 3/1999 |
| WO | 9209279 | 6/1992 |
| WO | 9818765 | 5/1998 |
| WO | 2004069394 | 8/2004 |
| WO | 2007097403 | 8/2007 |
| WO | 2010/098428 A1 | 9/2010 |

OTHER PUBLICATIONS

Alagille et al., "One-step synthesis of 2-arylbenzothiazole ('BTA') and—benzoxazole precursors for in vivo imaging of β-amyloid plaques", Tetrahedron Letters, 46:1349-1351 (2005).
Bellina et al., "Efficient and highly regioselective direct C-2 arylation of azoles, including free (NH)-imidazole, -benzimidazole and -indole, with aryl halides", Tetrahedron, 63:1970-1980 (2007).
Berman et al., "Rh(I)-Catalyzed Direct Arylation of Pyridines and Quinolines", J. Am. Chem. Soc., 130:14926-14927 (2008).
Do et al., "Copper-Catalyzed Arylation of Heterocycle C-H Bonds", J. Am. Chem. Soc., 129(41):12404-12405 (2007).
Fujita et al., "Direct arylation of aromatic C-H bonds catalyzed by Cp*Ir complexes", Chem. Comm., pp. 1926-1927 (2004).

(Continued)

Primary Examiner — Kamal Saeed
(74) Attorney, Agent, or Firm — Sughrue Mion, PLLC

(57) ABSTRACT

The present invention provides a method for producing a xanthine oxidase inhibitor, which is a therapeutic agent for hyperuricemia, or intermediates of the same, said method being efficient and using a short process. The present invention is a novel coupling method for obtaining a compound represented by formula (3) by bringing about a coupling reaction between a compound represented by formula (1) and a compound represented by formula (2), in the presence of a palladium compound, a ligand capable of coordinating to the palladium compound, a base, a $C_1$-$C_{40}$ carboxylic acid, and at least one kind of additive.

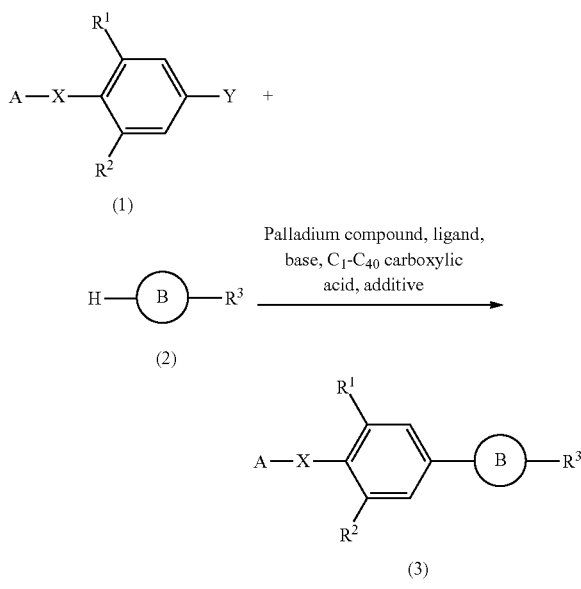

26 Claims, No Drawings

(56) References Cited

OTHER PUBLICATIONS

Hachiya et al., "Nickel-Catalyzed Direct Arylation of Azoles with Aryl Bromides", Org. Letters, 11(8):1737-1740 (2009).
Hasegawa, "A Facile One-Pot Synthesis of 4-alkoxy-1,3-benzenedicarbonitrile", Heterocycles, 47(2):857-864 (1998).
Huang et al., "A highly efficient palladium/copper cocatalytic system for direct arylation of heteroarenes: an unexpected effect of Cu(Xantphos)I", J. Am. Chem. Soc., 132:3674-3675 (2010).
Leclerc et al., "Palladium-Catalyzed Cross-coupling reactions of diazine N-oxides with aryl chlorides, bromides, and Iodides", Angew. Chem. Int. Ed., 45:7781-7786 (2006).
Liegault et al., "Establishment of Broadly Applicable Reaction Conditions for the Palladium-Catalyzed Direct Arylation of Heteroatom-Containing Aromatic Compounds", J. Org. Chem., 74:1826-1834 (2009).
Martin et al., "Direct C-2 arylation of alkyl 4-Thiazolecarboxylates: New insights in Synthesis of heterocyclic core of thiopeptide antibiotics", Org. Lett., 10(13):2909-2912 (2008).
Masui et al., "Synthesis and properties of donor-acceptor-type 2,5-diarylthiophene and 2,5-diarylthiazole", Org. Letters, 6(12):2011-2014 (2004).
Mori et al., "Facile Synthesis of 2,5-diarylthiazoles via palladium-catalyzed tandem C-H substitutions. Design of Tunable light emissions and liquid crystalline characteristics", J. Am. Chem. Soc., 125:1700-1701 (2003).
Nandurkar et al., "Palladium bis(2,2,6,6-tetramethyl-3,5-heptanedionate): an efficient catalyst for regioselective C-2 arylation of heterocycles", Tetrahedron Letters, 49:1045-1048 (2008).
Pivsa-Art et al., "Palladium-catalyzed arylation of azole compounds with aryl halides in the presence of alkali metal carbonates and the use of copper iodide in the reaction", Bull. Chem. Soc. Jpn., 71:467-473 (1998).
Sezen et al., "Cobalt-Catalyzed Arylation of Azole Heteroarenes via Direct C-H bond Functionalization", Organic Letters, 5(20):3607-3610 (2003).
Storr et al., "Pd(0)/Cu(I)-Mediated direct arylation of 2'-deoxyadenosines: Mechanistic role of Cu(I) and reactivity comparisons with related purine nucleosides", J. Org. Chem., 74:5810-5821 (2009).
Turner et al., "Direct arylation of thiazoles on Water", Angew. Chem. Int. Ed., 46:7996-8000 (2007).
Yokooji et al., "Palladium-catalyzed direct arylation of thiazoles with aryl bromides", Tetrahedron, 59:5685-5689 (2003).
Zhao et al., "Phosphine-Free, Palladium-Catalyzed Arylation of Heterocycles through C-H bond activation with Pivalic Acid as a cocatalyst", Chem. A Eur. J., 15:1337-1340 (2009).
Jerome Canivet, et al., "Nickel-Catalyzed Biaryl Coupling of Heteroarenes and Aryl Halides/Triflates", Organic Letters, 2009, pp. 1733-1736, vol. 11, No. 8.
Lutz Ackermann, "Transition-Metal-Catalyzed Direct Arylation of (Hetero)Arenes by C-H Bond Cleavage", Angew Chem Int Ed, 2009, pp. 9792-9826, vol. 48.
Marc Lafrance, "Palladium-Catalyzed Benzene Arylation: Incorporation of Catalytic Pivalic Acid as a Proton Shuttle and a Key Element in Catalyst Design", J Am Chem Soc, 2006, pp. 16496-16497, vol. 128.
Louis-Charles Campeau, et al., "Catalytic Direct Arylation with Aryl Chlorides, Bromides, and Iodides: Intramolecular Studies Leading to New Intermolecular Reactions", J Am Chem Soc, 2006, pp. 581-590, vol. 128.
Saha et al., "Palladium(0) nanoparticles-catalyzed ligand-free direct arylation of benzothiazole via C-H bond functionalization", Tetrahedron Letters, 51:5624-5627 (2010).
Martin et al., "Direct C-2 Arylation of alkyl 4-Thiazolecarboxylates: New Insights in Synthesis of heterocylcic core of thiopeptide antibiotics", Organic Letters, 10(13):2909-2912 (2008).
Communication for EP Application No. 11820025 dated Sep. 13, 2013, with Supplementary European Search Report (dated Sep. 6, 2013).

* cited by examiner

METHOD FOR PRODUCING PHENYL-SUBSTITUTED HETEROCYCLIC DERIVATIVE BY MEANS OF COUPLING METHOD USING PALLADIUM COMPOUND

CROSS REFERENCE TO RELATED APPLICATIONS

This application is a National Stage of International Application No. PCT/JP2011/069250, filed on Aug. 26, 2011, which claims priority from Japanese Patent Application No. 2010-190760, filed on Aug. 27, 2010, the contents of all of which are incorporated herein by reference in their entirety.

TECHNICAL FIELD

The present invention relates to a method for producing a phenyl-substituted heterocyclic derivative by using a novel coupling method between a phenyl derivative and a heterocyclic derivative. More particularly, the present invention relates to an excellent method for producing a phenyl-substituted heterocyclic derivative or an intermediate thereof, which is useful as a xanthine oxidase inhibitor used as a therapeutic agent for gout and/or hyperuricemia and the like.

BACKGROUND ART

The underlying disease of gout is hyperuricemia and, after remission from gout attacks, therapeutic modalities to improve hyperuricemia are performed. The therapeutic agents for hyperuricemia are broadly divided into a uricosuric drug and a uric acid synthesis inhibitor (xanthine oxidase inhibitor) and are selected appropriately depending on the status and degree of the disease.

The xanthine oxidase (XOD) inhibitors include 2-phenylthiazole derivatives (patent literature 1 to 6, non-patent literature 1), 3-phenylisothiazole derivatives (patent literature 7, 8), phenylpyrazole derivatives (patent literature 9 to 11), 2-phenyloxazole derivatives (patent literature 12), and phenylheteroaryl derivatives (patent literature 13). The methods of production disclosed in the patent literature 1 to 12 are those wherein heterocyclic rings are formed by linear consecutive reactions and thus, involve a large number of steps. The method of production disclosed in the patent literature 13 is a process wherein the skeleton is formed by direct coupling between a phenyl ring and a heterocyclic ring and, thus involves a small number of steps. However, this method needs to prepare boron compounds and thus results in a higher cost. Therefore, this method is not satisfactory in terms of a low-cost production method with a short process.

As a method of production by binding a heterocyclic ring directly to a phenyl ring at the position of C—H bond on the heterocyclic ring without using boron compounds, there have been reported methods of coupling reactions by using, as a catalyst, palladium compounds (non-patent literature 2 to 8), rhodium compounds (non-patent literature 9), iridium compounds (non-patent literature 10), copper compounds (non-patent literature 11), nickel compounds (non-patent literature 12 to 13), and cobalt compounds (non-patent literature 14). Among them, the method of production by using a nickel compound relates to a method for producing a phenyl-substituted heterocyclic derivative that is a xanthine oxidase (XOD) inhibitor (non-patent literature 12). However, no example has been reported wherein the phenyl-substituted heterocyclic derivative which is the target compound in the present invention was produced by using a metal catalyst other than nickel compounds. Moreover, none of the methods are satisfactory in terms of the restriction of substrate, cost, and yield.

The method of production which directly binds a heterocyclic ring to a phenyl ring at the position of C—H bond on the phenyl ring by using palladium compounds and copper compounds (non-patent literature 15 to 22), or a palladium compound and silver compounds (non-patent literature 23), is well known, but there are many examples wherein copper compounds and silver compounds that are not environmentally preferable are used in an amount equivalent or more to that of the substrate (non-patent literature 15 to 17, 23). In addition, even under the condition of not using the equivalent or more amount of the substrate (non-patent literature 18 to 22), the method is not satisfactory in terms of the restriction of substrate, cost, and yield.

Moreover, no example has been reported wherein the reaction rate is improved by using a palladium compound and a copper compound, or a palladium compound and a silver compound combined with a carboxylic acid.

CITATION LIST

Patent Literature

Patent literature 1: WO 92/009279 Pamphlet
Patent literature 2: Japanese Unexamined Patent Application Publication No. 6-293746
Patent literature 3: Japanese Unexamined Patent Application Publication No. 6-329647
Patent literature 4: Japanese Unexamined Patent Application Publication No. 6-345724
Patent literature 5: Japanese Unexamined Patent Application Publication No. 10-139770
Patent literature 6: Japanese Unexamined Patent Application Publication No. 11-60552
Patent literature 7: Japanese Unexamined Patent Application Publication No. 57-85379
Patent literature 8: Japanese Unexamined Patent Application Publication No. 6-211815
Patent literature 9: Japanese Unexamined Patent Application Publication No. 59-95272
Patent literature 10: WO 98/018765 Pamphlet
Patent literature 11: Japanese Unexamined Patent Application Publication No. 10-310578
Patent literature 12: Japanese Unexamined Patent Application Publication No. 6-65210
Patent literature 13: WO 2007/097403 Pamphlet

Non-patent Literature

Non-patent literature 1: Heterocycles 1998:47, 857
Non-patent literature 2: J. Am. Chem. Soc. 2006:128, 16496
Non-patent literature 3: J. Org. Chem. 2009:74, 1826
Non-patent literature 4: Org. Lett. 2008:10(13), 2909
Non-patent literature 5: Tetrahedron Letters 2008:49(6), 1045
Non-patent literature 6: Tetrahedron 2003:59(30), 5685
Non-patent literature 7: Chem. A. Eur. J. 2009:15(6), 1337
Non-patent literature 8: J. Am. Chem. Soc. 2006:128(2), 581
Non-patent literature 9: J. Am. Chem. Soc. 2008:130, 14926
Non-patent literature 10: Chem. Comm. 2004:1926
Non-patent literature 11: J. Am. Chem. Soc. 2007:129(41), 12404
Non-patent literature 12: Org. Lett. 2009:11(8), 1733

Non-patent literature 13: Org. Lett. 2009:11(8), 1737
Non-patent literature 14: Org. Lett. 2003:5(20), 3607
Non-patent literature 15: Tetrahedron 2007:63(9), 1970
Non-patent literature 16: J. Org. Chem. 2009:74, 5810
Non-patent literature 17: Bull. Chem. Soc. Jpn. 1998:71, 467
Non-patent literature 18: Org. Lett. 2004: 6(12), 2011
Non-patent literature 19: J. Am. Chem. Soc. 2010: 132, 3674
Non-patent literature 20: Angew. Chem. Int. Ed. 2006: 7781
Non-patent literature 21: Tetrahedron Letters 2005: 46(8), 1349
Non-patent literature 22: J. Am. Chem. Soc. 2003: 125, 1700
Non-patent literature 23: Angew. Chem. Int. Ed. 2007: 46, 7996

DISCLOSURE OF THE INVENTION

Technical Problem

The object of the present invention is to provide an excellent method of production involving short process, which is different from the heretofore publicly known methods, for a phenyl-substituted heterocyclic derivative or intermediates thereof, which is a xanthine oxidase inhibitor used as a therapeutic agent for gout and/or hyperuricemia and the like.

Means for Solving the Problem

As a result of extensive efforts and investigation to solve the above-mentioned problems, the inventors have attained the finding that the phenyl ring of a phenyl derivative and a heterocyclic derivative at the position of C—H bond on the heterocyclic ring can be directly coupled and a desired coupling reaction progresses with high substrate selectivity by using;
(i) a palladium compound,
(ii) a ligand capable of coordinating to the palladium compound or a salt thereof,
(iii) a base,
(iv) a $C_1$ to $C_{40}$ carboxylic acid or a salt thereof, and
(v) at least one additive selected from the group consisting of copper, silver, and salts thereof, and complexes thereof.
Accordingly, the present invention relates to:
[1] A method comprising reacting
a compound represented by the following formula (1)

Compound 1

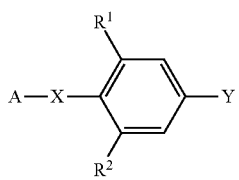

(1)

wherein in formula (1)
$R^1$ represents a hydrogen atom or a halogen atom;
$R^2$ represents a hydrogen atom, a cyano group, a nitro group, a halogen atom, a formyl group, or a halomethyl group;
A represents a hydrogen atom, a $C_1$ to $C_8$ alkyl group, a $C_3$ to $C_6$ cycloalkyl group, a phenyl group, a fluorine atom (only when X is a bond), or a protecting group for a hydroxyl group (only when X is an oxygen atom),
wherein A may be substituted with 1 to 3 substituents, such substituents are a group selected from the group consisting of a halogen atom, a $C_1$ to $C_4$ alkyl group, a $C_1$ to $C_4$ alkoxy group, a $C_1$ to $C_4$ alkylthio group, a $C_3$ to $C_6$ cycloalkyl group, a phenyl group, a phenoxy group, and a pyridyl group;
X represents a bond (only when A is a phenyl group or a fluorine atom), or an oxygen atom; and Y represents a leaving group); and
a compound represented by the following formula (2)

Compound 2

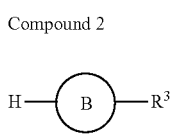

(2)

wherein in formula (2)
H represents a hydrogen atom; and
B represents a group selected from the following formulae;

Compound 3

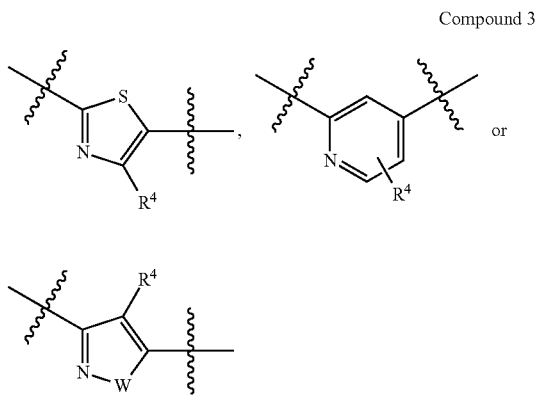

$R^3$ represents —COOR$^{3a}$ or —COR$^{3b}$;
$R^{3a}$ represents a hydrogen atom, a $C_1$ to $C_4$ alkyl group or an ester-type protecting group for a carboxyl group;
$R^{3b}$ represents an amide-type protecting group for a carboxyl group, wherein the protecting group forms an amide with an adjacent carbonyl group;
$R^4$ represents a hydrogen atom, a halogen atom or a $C_1$ to $C_4$ alkyl group; and
W represents an oxygen atom or a sulfur atom);
in the presence of
(i) a palladium compound,
(ii) a ligand capable of coordinating to the palladium compound or a salt thereof,
(iii) a base,
(iv) a $C_1$ to $C_{40}$ carboxylic acid or a salt thereof, and
(v) at least one additive selected from the group consisting of copper, silver, salts thereof, and complexes thereof to produce a phenyl-substituted heterocyclic derivative represented by the following formula (3);

Compound 4

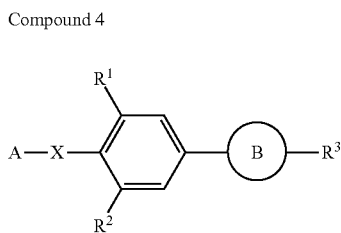

(3)

wherein in formula (3)
the definition of A, X, $R^1$, and $R^2$ is the same as those defined in formula (1), the definition of B and $R^3$ is the same as in formula (2)).

[2] The method of production according to [1], wherein A is a $C_1$ to $C_5$ alkyl group.

[3] The method of production according to [1], wherein A is an isobutyl group.

[4] The method of production according to any one of [1] to [3], wherein X is an oxygen atom.

[5] The method of production according to any one of [1] to [4], wherein $R^1$ is a hydrogen atom.

[6] The method of production according to any one of [1] to [5], wherein $R^2$ is a cyano group.

[7] The production method according to any one of [1] to [6], wherein Y is a halogen atom, —$OCO_2$—($C_1$ to $C_4$ alkyl group), —$OCO_2$—(phenyl group), —$OSO_2$—($C_1$ to $C_4$ alkyl group), —$OSO_2$-(phenyl group), or diazonium group, wherein, in Y, the $C_1$ to $C_4$ alkyl group may be substituted with 1 to 3 halogen atoms and the phenyl group may be substituted with 1 to 5 optional substituents selected from halogen atoms and $C_1$ to $C_4$ alkyl groups.

[8] The method of production according to any one of [1] to [7], wherein B is represented by the following group.

Compound 5

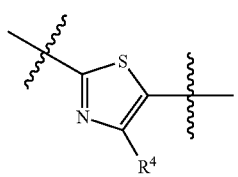

[9] The method of production according to any one of [1] to [8], wherein $R^3$ is $COOR^{3a}$ and $R^{3a}$ is a $C_1$ to $C_4$ alkyl group.

[10] The method of production according to any one of [1] to [9], wherein $R^4$ is a methyl group.

[11] The method of production according to any one of [1] to [10], wherein the palladium compound is zerovalent palladium, or a salt of monovalent or divalent palladium.

[12] The method of production according to any one of [1] to [10], wherein the palladium compound is zerovalent palladium or a salt of divalent palladium.

[13] The method of production according to any one of [1] to [10], wherein the palladium compound is palladium(II) acetate (Pd(OAc)$_2$), palladium(II) propionate (Pd(O(C═O)CH$_2$CH$_3$)$_2$), palladium(II) 2-methylpropanoate (Pd(O(C═O)CH(CH$_3$)$_2$)$_2$), palladium(II) pivalate (Pd(OPiv)$_2$), palladium(II) 1-adamantanecarboxylate, palladium(II) chloride (PdCl$_2$), palladium(I) bromide (Pd$_2$Br$_2$), palladium(II) bromide (PdBr$_2$), or palladium(0).

[14] The method of production according to any one of [1] to [10], wherein the palladium compound is palladium(II) acetate (Pd(OAc)$_2$), palladium(II) propionate (Pd(O(C═O)CH$_2$CH$_3$)$_2$), palladium(II) 2-methylpropanoate (Pd(O(C═O)CH(CH$_3$)$_2$)$_2$), palladium(II) pivalate (Pd(OPiv)$_2$), palladium(II) chloride (PdCl$_2$), palladium(II) bromide (PdBr$_2$), or palladium(0).

[15] The method of production according to any one of [1] to [10], wherein the palladium compound is palladium(II) 2-methylpropanoate (Pd(O(C═O)CH(CH$_3$)$_2$)$_2$), palladium pivalate (Pd(OPiv)$_2$), palladium(II) chloride (PdCl$_2$), palladium(II) bromide (PdBr$_2$), or palladium(0).

[16] The method of production according to any one of [1] to [13], wherein the ligand is a phosphine-type ligand.

[17] The method of production according to any one of [1] to [16], wherein the ligand is a phosphine-type ligand represented by $R^5P(R^6)R^7$ ($R^5$, $R^6$, and $R^7$ represent each independently a $C_1$ to $C_8$ alkyl group, a $C_1$ to $C_4$ alkoxy group, an alicyclic hydrocarbon group, a $C_6$ to $C_{12}$ aryl group, a heteroaryl group, a $C_6$ to $C_{12}$ aryloxy group, or heteroaryloxy group, and $R^5$ and $R^6$ may bind together to form a $C_2$ to $C_8$ alkylene group).

[18] The method of production according to [17], wherein as for the phosphine-type ligand represented by $R^5P(R^6)R^7$, $R^5$ and $R^6$ represent each independently a $C_3$ to $C_8$ alkyl group or an alicyclic hydrocarbon group, and $R^7$ represents a $C_1$ to $C_8$ alkyl group, alicyclic hydrocarbon group, a $C_6$ to $C_{12}$ aryl group or a heteroaryl group.

[19] The method of production according to [18], wherein as for the phosphine-type ligand represented by $R^5P(R^6)R^7$, the number of hydrogen atoms bonded to each carbon atom of $R^5$ and $R^6$ is 0 or 1, wherein $R^5$ and $R^6$ are bonded to a phosphorus atom.

[20] The method of production according to [19], wherein $R^7$ is a $C_3$ to $C_8$ alkyl group or an alicyclic hydrocarbon group.

[21] The method of production according to any of [1] to [16], wherein the ligand is tri(tert-butyl)phosphine, di(tert-butyl)methylphosphine, di(tert-butyl)cyclohexylphosphine, tert-butyldicyclohexylphosphine, or tri(cyclohexyl)phosphine.

[22] The method of production according to any one of [1] to [16], wherein the ligand is di(tert-butyl)cyclohexylphosphine.

[23] The method of production according to any one of [1] to [16], wherein the ligand is a phosphine-type ligand represented by $R^8(R^9)PR^{10}P(R^{11})R^{12}$ or an amine-phosphine-type ligand represented by $R^8(R^9)PR^{10}N(R^{11})R^{12}$, wherein $R^8$, $R^9$, $R^{11}$, and $R^{12}$ represent each independently a $C_1$ to $C_8$ alkyl group, a $C_1$ to $C_4$ alkoxy group, an alicyclic hydrocarbon group, a $C_6$ to $C_{12}$ aryl group, a heteroaryl group, a $C_6$ to $C_{12}$ aryloxy group, or a heteroaryloxy group;

$R^{10}$ represents a $C_1$ to $C_3$ alkylene group, a divalent alicyclic hydrocarbon group, a $C_6$ to $C_{12}$ arylene group, or a heteroarylene group; and the nitrogen atom bonded to $R^{11}$ and $R^{12}$, $R^{11}$, and $R^{12}$ may form a heteroaryl group together when, $R^{11}$ and $R^{12}$ are bonded to the nitrogen atom.

[24] The method of production according to [23], wherein $R^8$ and $R^9$ are each independently a $C_3$ to $C_8$ alkyl group or alicyclic hydrocarbon group in the phosphine-type ligand represented by $R^8(R^9)PR^{10}P(R^{11})R^{12}$ or the amine-phosphine-type ligand represented by $R^8(R^9)PR^{10}N(R^{11})R^{12}$.

[25] The method of production according to [24], wherein the number of hydrogen atoms bonded to each carbon atom of $R^8$ or $R^9$ is 0 or 1, wherein $R^8$ and $R^9$ are bonded to the phosphorus atom or the nitrogen atom in the phosphine-type ligand represented by $R^8(R^9)PR^{10}P(R^{11})R^{12}$ or the amine-phosphine-type ligand represented by $R^8(R^9)PR^{10}N(R^{11})R^{12}$.

[26] The method of production according to any one of [1] to [25], wherein the base is a hydroxide of an alkali metal or a Group 2 element, a fluoride of an alkali metal, a phosphate of an alkali metal, or a carbonate or a hydrogen carbonate of an alkali metal or a Group 2 element.

[27] The method of production according to any one of [1] to [25], wherein the base is a carbonate or a hydrogen carbonate of an alkali metal.

[28] The method of production according to any one of [1] to [25], wherein the base is potassium carbonate, potassium hydrogen carbonate, cesium carbonate, sodium carbonate, or sodium hydrogen carbonate.

[29] The method of production according to any one of [1] to [25], wherein the base is potassium carbonate, potassium hydrogen carbonate, sodium carbonate, or sodium hydrogen carbonate.

[30] The method of production according to any one of [1] to [25], wherein the base is potassium carbonate or potassium hydrogen carbonate.

[31] The method of production according to any one of [1] to [30], wherein the carbon atom of the carboxyl group at the α-position in the $C_1$ to $C_{40}$ carboxylic acid is not the carbon atom on the aromatic ring.

[32] The method of production according to any one of [1] to [31], wherein the number of hydrogen atoms bonded to the carbon atom of the carboxyl group at the α-position in the $C_1$ to $C_o$ carboxylic acid is 0 or 1.

[33] The method of production according to any one of [1] to [32], wherein the $C_1$ to $C_{40}$ carboxylic acid contains one carboxyl group.

[34] The method of production according to any one of [1] to [33], wherein the $C_1$ to $C_{40}$ carboxylic acid consists of only carbon atoms and hydrogen atoms as constituent atoms except the carboxyl group.

[35] The method of production according to any one of [1] to [34], wherein the carboxylic acid is a $C_1$ to $C_{12}$ carboxylic acid.

[36] The method of production according to any one of [1] to [30], wherein the carboxylic acid is 2-methylpropanoic acid or pivalic acid.

[37] The method of production according to any one of [1] to [36], wherein a divalent palladium salt of a $C_1$ to $C_{40}$ carboxylic acid is used instead of using (i) the palladium compound and (iv) the $C_1$ to $C_{40}$ carboxylic acid or a salt thereof independently.

[38] The method of production according to any one of [1] to [36], wherein a monovalent copper salt or a monovalent silver salt of a $C_1$ to $C_{40}$ carboxylic acid is used instead of using (iv) the $C_1$ to $C_{40}$ carboxylic acid or a salt thereof and (v) the additive independently.

[39] The method of production according to any one of [1] to [37], wherein the additive is zerovalent copper or a monovalent copper salt.

[40] The method of production according to any one of [1] to [38], wherein the additive is at least one additive selected from the group consisting of copper(I) oxide, copper(I) fluoride, copper(I) chloride, copper(I) bromide, copper(I) iodide, copper(I) formate, copper(I) acetate, copper(I) propionate, copper(I) 2-methylpropanoate, copper(I) 2-ethylbutanoate, copper(I) 2-methylbutanoate, copper(I) 2-methylpentanoate, copper(I) 2-methylhexanoate, copper(I) 2-methylheptanoate, copper(I) 2,2-dimethylbutanoate, copper(I) 2,3-dimethylbutanoate, copper(I) 2,2-dimethylpentanoate, copper(I) 2,3,3-trimethylbutanoate, copper(I) 2-ethylhexanoate, copper(I) 2,2-diethylbutanoate, copper(I) 2,2,4-trimethylpentanoate, copper(I) 2-methyloctanoate, copper(I) 2-methylundecanoate, copper(I) 2-methylnonanoate, copper(I) pivalate, copper(I) cyclopropanoate, copper(I) 2,2,3,3-tetramethylcyclopropanoate, copper(I) cyclopentanoate, and copper(I) 1-adamantanecarboxylate.

[41] The method of production according to any one of [1] to [38], wherein the additive is at least one additive selected from the group consisting of copper(I) chloride, copper(I) bromide, copper(I) 2-methylpropanoate, and copper(I) pivalate.

[42] The method of production according to any one of [1] to [38], wherein the additive is zerovalent silver or a monovalent silver salt.

[43] The method of production according to any one of [1] to [38], wherein the additive is at least one additive selected from the group consisting of silver(I) oxide, silver(I) fluoride, silver(I) chloride, silver(I) bromide, silver(I) iodide, silver(I) formate, silver(I) acetate, silver(I) propionate, silver(I) 2-methylpropanoate, silver(I) 2-ethylbutanoate, silver(I) 2-methylbutanoate, silver(I) 2-methylpentanoate, silver(I) 2-methylhexanoate, silver(I) 2-methylheptanoate, silver(I) 2,2-dimethylbutanoate, silver(I) 2,3-dimethylbutanoate, silver(I) 2,2-dimethylpentanoate, silver(I) 2,3,3-trimethylbutanoate, silver(I) 2-ethylhexanoate, silver(I) 2,2-diethylbutanoate, silver(I) 2,2,4-trimethylpentanoate, silver(I) 2-methyloctanoate, silver(I) 2-methylundecanoate, silver(I) 2-methylnonanoate, silver(I) pivalate, silver(I) cyclopropanoate, silver(I) 2,2,3,3-tetramethylcyclopropanoate, silver(I) cyclopentanoate, and silver(I) 1-adamantanecarboxylate.

[44] The method of production according to any one of [1] to [38], wherein the additive is at least one additive selected from the group consisting of silver(I) chloride, silver(I) bromide, silver(I) 2-methylpropanoate, and silver(I) pivalate.

[45] The method of production according to any one of [1] to [44], wherein a solvent further exists in the course of the reaction.

[46] The method of production according to [45], wherein the solvent is at least one solvent selected from the group consisting of aliphatic hydrocarbons (pentane, hexane, heptane, octane, nonane, decane, undecane, dodecane, cyclohexane, cycloheptane, cyclooctane, and the like), aromatic hydrocarbons (toluene, xylene, mesitylene, chlorobenzene and the like), ethers (dimethoxyethane, cyclopentyl methyl ether, tert-butyl methyl ether, tetrahydrofuran, diethylene glycol dimethyl ether, and the like), ketones (acetone, methyl isobutyl ketone, and the like), esters (butyl acetate, ethyl propionate, and the like), and mixed solvents thereof.

Advantageous Effects of Invention

According to the present invention, by selectively coupling a phenyl derivative (a compound represented by formula (1)) and a heterocyclic derivative (a compound represented by formula (2)) together in the presence of a palladium compound, a ligand capable of coordinating to the palladium compound, a base, a $C_1$ to $C_{40}$ carboxylic acid, and one or more additives, a phenyl-substituted heterocyclic derivative (a compound represented by formula (3)) can be obtained in a short process.

Furthermore, the phenyl-substituted heterocyclic derivative (the compound represented by formula (3)) can be produced in high yield and at low cost since the method of production involves a short process.

DESCRIPTION OF EMBODIMENTS

The terms used alone or in combination in the present description will be explained in the following. Explanation of each substituent shall be common to each part unless otherwise indicated. In addition, combinations of substituents and variables are allowed only when such combinations give a chemically stable compound. When the substituent itself is substituted with two or more groups, these many groups can exist in the same or different carbon atom to the extent that a stable structure is formed.

In the present invention, the term "halogen atom" means a fluorine atom, a chlorine atom, a bromine atom, and an iodine atom.

In the present invention, the term "$C_1$ to $C_8$ alkyl group" means a linear or branched saturated aliphatic hydrocarbon group having 1 to 8 carbon atoms and includes, for example, a methyl group, an ethyl group, a n-propyl group, an isopropyl group, a n-butyl group, an isobutyl group, a tert-butyl group, a n-pentyl group, an isopentyl group, a neopentyl group, a 1-methylpropyl group, a n-hexyl group, an isohexyl group, a 1,1-dimethylbutyl group, a 2,2-dimethylbutyl group, a 3,3-dimethylbutyl group, a n-heptyl group, a n-octyl group, and the like.

In the present invention, for example, the term "C" such as "$C_1$" and the like mean a carbon atom and the following numeral indicates the number of the carbon atoms. For example, the term "$C_1$ to $C_6$" means a range of the number of carbon atoms from 1 to 6. Needless to say, in the present invention, when the number of carbon atoms is different, it means the group having the number of carbon atoms with the specified number. For example, the term "$C_1$ to $C_4$ alkyl group" means alkyl having 1 to 4 carbon atoms in the explanation of the "$C_1$ to $C_8$ alkyl group". The number of carbon atoms in the other groups is handled in the same rule.

In the present invention, the term "$C_1$ to $C_4$ alkoxy group" means a group consisting of a "$C_1$ to $C_4$ alkyl group" and an oxy group and includes, for example, a methoxy group, an ethoxy group, a n-propyloxy group, an isopropyloxy group, a n-butyloxy group, an isobutyloxy group, a tert-butyloxy group, and the like.

In the present invention, the term "alicyclic hydrocarbon group" means a saturated alicyclic hydrocarbon group having 3 to 12 carbon atoms wherein the carbon ring is monocyclic, bicyclic or tricyclic. The examples involve a cyclopropyl group, a cyclobutyl group, a cyclopentyl group, a cyclohexyl group, a cycloheptyl group, a cyclooctyl group, a 1-norbornyl group, a 2-norbornyl group, a 7-norbornyl group, a 1-adamantyl group, a 2-adamantyl group, a 3-noradamantyl group, and the like.

In the present invention, the term "$C_3$ to $C_8$ cycloalkyl group" means a monocyclic alicyclic hydrocarbon group having 3 to 8 carbon atoms among all the "alicyclic hydrocarbon groups" and includes, for example, a cyclopropyl group, a cyclobutyl group, a cyclopentyl group, a cyclohexyl group, a cycloheptyl group, a cyclooctyl group, and the like.

In the present invention, the term "$C_1$ to $C_8$ alkylene group" means a divalent group of a saturated linear or branched aliphatic hydrocarbon group having 1 to 8 carbon atoms and includes, for example, a methylene group, an ethylene group, a n-propylene group, a n-butylene group, a n-pentylene group, a 1-methylpropylene group, a n-hexylene group, an isohexylene group, a 1,1-dimethylbutylene group, a 2,2-dimethylbutylene group, a 1,3-dimethylbutylene group, a n-heptylene group, a n-octylene group, and the like.

In the present invention, the term "divalent alicyclic hydrocarbon group" means a divalent group of an alicyclic hydrocarbon group having 3 to 12 carbon atoms wherein the carbon ring is saturated monocyclic, bicyclic or tricyclic. Example includes a cyclopropylene group, a cyclobutylene group, a cyclopentylene group, a cyclohexylene group, a cycloheptylene group, a cyclooctylene group, a norbornylene group, a noradamantylene group, and the like.

In the present invention, the term "$C_3$ to $C_8$ cycloalkylene group" means a divalent group of a monocyclic alicyclic hydrocarbon group having 3 to 8 carbon atoms among all the "divalent alicyclic hydrocarbon groups" and includes, for example, a cyclopropylene group, a cyclobutylene group, a cyclopentylene group, a cyclohexylene group, a cycloheptylene group, a cyclooctylene group, and the like.

In the present invention, the term "$C_6$ to $C_{12}$ aryl group" means a functional group formed by eliminating one hydrogen atom bonded to the carbon atom on the ring of an aromatic hydrocarbon having 6 to 12 carbon atoms and includes, for example, a phenyl group, a biphenyl group, a naphthyl group, and the like.

In the present invention, the term "heteroaryl group" means a functional group formed by eliminating one hydrogen atom from a 5- to 12-membered aromatic heterocycle having 1 to 4 hetero atoms selected from the group consisting of an oxygen atom, a sulfur atom, a nitrogen atom and includes, for example, a furyl group, a thiofuryl group, a pyrrolyl group, an imidazoryl group, a pyrazolyl group, a thiazolyl group, an oxazolyl group, an indolyl group, a benzothiazolyl group, a benzimidazolyl group, a benzoxazolyl group, a triazolyl group, a tetrazolyl group, a pyridyl group, and the like.

In the present invention, the term "$C_6$ to $C_{12}$ aryloxy group" means a group consisting of a "$C_6$ to $C_{12}$ aryl group" and an oxy group and includes, for example, a phenoxy group, a biphenoxy group, a naphthoxy group and, the like.

In the present invention, the term "heteroaryloxy group" means a group consisting of a "heteroaryl group" and an oxy group and includes, for example, a furyloxy group, a thiofuryloxy group, a pyrroloxy group, an imidazoloxy group, a pyrazoloxy group, a thiazoloxy group, an oxazoloxy group, an indoleoxy group, a benzothiazoloxy group, a benzimidazoloxy group, a benzoxazoloxy group, a triazoleoxy group, a tetrazoleoxy group, a pyridinoxy group, and the like.

In the present invention, the term "$C_6$ to $C_{12}$ arylene group" means a divalent functional group formed by eliminating two hydrogen atoms bonded to the carbon atom of the aromatic hydrocarbon having 6 to 12 carbon atoms and includes, for example, a phenylene group, a biphenylene group, a naphthylene, and the like.

In the present invention, the term "heteroarylene group" means a functional group formed by eliminating two hydrogen atoms from a 5- to 12-membered aromatic heterocycle having 1 to 4 hetero atoms selected from the group consisting of an oxygen atom, a sulfur atom, and a nitrogen atom and includes, for example, a furylene group, a thiofurylene group, a pyrrolylene group, an imidazolylene group, a pyrazolylene group, a thiazolylene group, an oxazolylene group, an indolylene group, a benzothiazolylene group, a benzimidazolylene group, a benzoxazolylene group, a triazolylene group, a pyridylene group, and the like.

In the present invention, the term "$C_1$ to $C_4$ alkylthio group" means a group consisting of a "$C_1$ to $C_4$ alkyl group" and a thio group and includes, for example, a methylthio group, an ethylthio group, a n-propylthio group, an isopropylthio group, a n-butylthio group, an isobutylthio group, a tert-butylthio group, and the like.

In the present invention, the "$C_1$ to $C_8$ alkyl group", the "$C_1$ to $C_4$ alkoxy group", the "alicyclic hydrocarbon group", the "divalent alicyclic hydrocarbon group", the "$C_6$ to $C_{12}$ aryl group", the "heteroaryl group", the "$C_6$ to $C_{12}$ aryloxy group", the "heteroaryloxy group", the "$C_6$ to $C_{12}$ arylene group", and the "heteroarylene group" existing in the phosphine-type ligand represented by $R^5P(R^6)R^7$ or $R^8(R^9)PR^{10}P$ ($R^{11}$)$R^{12}$, the amine-phosphine-type ligand represented by $R^8(R^9)PR^{10}N(R^{11})R^{12}$, or the amine-type ligand represented by $R^8(R^9)NR^{10}N(R^{11})R^{12}$ may be substituted with 1 to 4 groups selected from the group consisting of a halogen atom, a $C_1$ to $C_4$ alkyl group, a $C_1$ to $C_4$ alkoxy group, a $C_6$ to $C_{12}$ aryl group, a heteroaryl group, a $C_6$ to $C_{12}$ aryloxy group, a heteroaryloxy group, a primary amino group, a secondary amino group, a halomethyl group, and the like.

In the present invention, the term "primary amino group" means a functional group wherein a group selected from the group consisting of "a $C_1$ to $C_4$ alkyl group, an alicyclic hydrocarbon group, a $C_6$ to $C_{12}$ aryl group, and a heteroaryl group" and a hydrogen atom are bonded to the nitrogen atom of the amino group and includes, for example, a methylamino group, an ethylamino group, a n-propylamino group, an iso-propylamino group, a n-butylamino group, an isobutylamino group, a tert-butylamino group, a cyclopropylamino group, a cyclobutylamino group, a cyclopentylamino group, a cyclohexylamino group, a cycloheptylamino group, a cyclooctylamino group, a 1-norbornylamino group, a 2-norbornylamino group, a 7-norbornylamino group, a 1-adamantylamino group, a 2-adamantylamino group, a 3-noradamantylamino group, an anilino group, a biphenylamino group, a naphtylamino group, a furylamino group, a thiofurylamino group, a pyrrolylamino group, an imidazolylamino group, a pyrazolylamino group, a thiazolylamino group, an oxazolylamino group, an indolylamino group, a benzothiazolylamino group, a benzimidazolylamino group, a benzoxazolylamino group, a triazolylamino group, a tetrazolylamino group, a pyridylamino group, and the like.

In the present invention, the term "secondary amino group" means a functional group wherein two groups independently selected from the group consisting of "a $C_1$ to $C_4$ alkyl group, an alicyclic hydrocarbon group, a $C_6$ to $C_{12}$ aryl group, and a heteroaryl group" are bonded to the nitrogen atom of the amino group or "a $C_1$ to $C_8$ alkylene group" is bonded to the nitrogen atom of the amino group by its two bonds independently.

In the secondary amino group, there are cited examples of the functional group wherein two groups independently selected from the group consisting of the "a $C_1$ to $C_4$ alkyl group, an alicyclic hydrocarbon group, a $C_6$ to $C_{12}$ aryl group, and a heteroaryl group" are bonded to the nitrogen atom of the amino group include a diethylamino group, a diisopropylamino group, a di(n-butyl)amino group, a diisobutylamino group, a di-tert-butylamino group, an ethylmethylamino group, an ethylisopropylamino group, a dicyclopropylamino group, a dicyclobutylamino group, a dicyclopentylamino group, a dicyclohexylamino group, a dicycloheptylamino group, a dicyclooctylamino group, a cyclopropylmethylamino group, a cyclohexylmethylamino group, a cyclopentylethylamino group, a cyclooctyl(n-propyl)amino group, a methyl-1-norbornylamino group, an ethyl-2-norbornylamino group, a n-propyl-7-norbornylamino group, an isopropyl-1-adamantylamino group, an isobutyl-2-adamantylamino group, a cyclopropyl-3-noradamantylamino group, a diphenylamino group, a biphenylphenylamino group, a naphtylphenylamino group, a difurylamino group, a dithiofurylamino group, a dipyrrolylamino group, a diimidazolylamino group, a dipyrazolylamino group, a dithiazolylamino group, a dioxazolylamino group, a diindolylamino group, a dibenzothiazolylamino group, a dibenzimidazolylamino group, a dibenzoxazolylamino group, a ditriazolylamino group, a ditetrazolylamino group, a dipyridylamino group, and the like.

There are cited examples of the functional group wherein the "$C_1$ to $C_8$ alkylene group" is bonded to the nitrogen atom of the amino group by its two bonds independently include an aziridino group, an azetidino group, a pyrrolidino group, a piperidino group, and the like.

In the present invention, the term "heteroarene" means a 5- to 12-membered aromatic heterocyclic compound having 1 to 4 hetero atoms selected from the group consisting of an oxygen atom, a sulfur atom, and a nitrogen atom and includes, for example, furan, thiofuran, pyran, imidazole, pyrazole, oxazole, indole, benzothiazole, benzimidazole, benzoxazole, triazole, tetrazole, pyridine, and the like. The heteroarene is used as a monodentate or bidentate ligand in the present invention. The heteroarene may be substituted with 1 to 3 substitutes selected from the group consisting of a halogen atom, a $C_1$ to $C_4$ alkyl group, a $C_1$ to $C_4$ alkoxy group, a $C_6$ to $C_{12}$ aryl group, a heteroaryl group, a $C_6$ to $C_{12}$ aryloxy group, a heteroaryloxy group, a primary amino group, a secondary amino group, a halomethyl group, and the like.

In the present invention, the term "halomethyl group" means a methyl group substituted with 1 to 3 halogen atoms and includes, for example, a trifluoromethyl group, a difluoromethyl group, a fluoromethyl group, a trichloromethyl group, a dichloromethyl group, a chloromethyl group, a tribromomethyl group, a dibromomethyl group, a bromomethyl group, and the like.

In the present invention, the term "leaving group" means an atom or a group of atoms, which is detached from the reaction substrate in substitution reactions, elimination reactions, or the like. Examples of such a "leaving group" include, a halogen atom, —$OCO_2$—($C_1$ to $C_4$ alkyl group), —$OCO_2$—(phenyl group), —$OSO_2$—($C_1$ to $C_4$ alkyl group), —$OSO_2$—(phenyl group), a diazonium group (—$N^+\equiv N$), or the like. In addition, the $C_1$ to $C_4$ alkyl group that constitutes the leaving group may be substituted with 1 to 3 halogen atoms and the phenyl group that constitutes the leaving group may be substituted with 1 to 5 optional substituents selected from the group consisting of a halogen atom or $C_1$ to $C_4$ alkyl group. However, it is not limited to those.

The term "protecting group for a hydroxyl group" means a group which protects a hydroxyl group. Such a "protecting group for a hydroxyl group" is well known in the art and is classified into an ether-type protecting group, a silyl ether-type protecting group, an ester-type protecting group, a carbonate-type protecting group, a phosphine-type protecting group, a sulfonate-type protecting group, and the like. Examples include a protecting group for phenol described in "Protective Groups in Organic Synthesis (3rd Ed., 1994), (4th Ed., 2006)" by T. W. Greene and P. G. M. Wuts, and the like, such as a benzyloxymethyl group, a methoxyethoxymethyl group, a phenylthiomethyl group, a phenacylmethyl group, a 4-bromophenacylmethyl group, a cyclopropylmethyl group, an allyl group, a propargyl group, a cyclohexyl group, a benzyl group, an o-nitrobenzyl group, a 4-(dimethylamino) carbonylbenzyl group, a 4-methylsulfinylbenzyl group, a 9-anthranylmethyl group, a 4-picolyl group, a trimethylsilyl group, a tert-butyldimethylsilyl group, a tert-butyldiphenylsilyl group, a triisopropylsilyl group, a formyl group, —(C=O)—($C_1$ to $C_4$ alkyl group), a benzoyl group, a 4-oxopentanoyl group, a pivaloyl group, a methylester group, a 1-adamantyloxycarbonyl group, a tert-butoxycarbonyl group, a 4-methylsulfinylbenzyloxycarbonyl group, a 2,4-dimethylpent-3-yloxycarbonyl group, a 2,2,2-trichloroethoxycarbonyl group, a vinyloxycarbonyl group, a benzyloxycarbonyl group, —(C=O)NH—($C_1$ to $C_4$ alkyl group), a methanesulfonyl group, a toluenesulfonyl group, and the like. However, the present invention is not limited to the groups exemplified herein and any group may be selected as long as it can be employed as the protecting group for the hydroxyl group. Herein, the protecting group for the hydroxyl group as A is employed as the protecting group for the hydroxyl group when X is an oxygen atom. For example, when a benzyl group is the protecting group, A-X- corresponds to $PhCH_2$—O—.

In the present invention, the term "ester-type protecting group for a carboxyl group" means a group that protects the carboxyl group by binding with an oxygen atom of the carboxyl group to be protected and form an ester. Such an "ester-type protecting group for a carboxyl group" includes groups described as an ester-type protecting group for the carboxyl group described in "Protective Groups in Organic Synthesis (3rd Ed., 1994), (4th Ed., 2006)" by T. W Greene and P. G. M. Wuts, such as a $C_1$ to $C_6$ alkyl group, a 9-fluorenylmethyl group, a methoxymethyl group, a methylthiomethyl group, a tetrahydropyranyl group, a tetrahydrofuranyl group, a methoxyethoxymethyl group, a 2-(trimethylsilyl)ethoxymethyl group, a benzyloxymethyl group, a pivaloyloxymethyl group, a phenylacetoxymethyl group, a triisopropylsilylmethyl group, a p-bromophenacyl group, an α-methylphenacyl group, a p-methoxyphenacyl group, a decyl group, a carboxamidomethyl group, a p-azobenzenecarboxamidomethyl group, an N-phthalimidomethyl group, a 2,2,2-trichloroethyl group, a 2-haloethyl group, an ω-chloroalkyl group, a 2-(triethylsilyl)ethyl group, a 2-methylthioethyl group, a 1,3-dithianyl-2-methyl group, a 2-(p-nitrophenylsulfenyl)ethyl group, a 2-(p-toluenesulfonyl)ethyl group, a 2-(2'-pyridyl) ethyl group, a 2-(p-methoxyphenyl)ethyl group, a 2-(diphenylphosphino)ethyl group, a 1-methyl-1-phenylethyl group, a 2-(4-acetyl-2-nitrophenyl)ethyl group, a 2-cyanoethyl group, a dicyclopropylmethyl group, a cyclopentyl group, a cyclohexyl group, an allyl group, a methallyl group, a 2-methylbut-3-en-2-yl group, a 3-methylbut-2-enyl (or prenyl) group, a 3-buten-1-yl group, a 4-(trimethylsilyl)-2-buten-1-yl group, a cinnamyl group, an α-methylcinnamyl group, a prop-2-ynyl (or propargyl) group, a phenyl group, a 2,6-dimethylphenyl group, a 2,6-diisopropylphenyl group, a 2,6-di(tert-butyl)-4-methylphenyl group, a 2,6-di(tert-butyl)-4-methoxyphenyl group, a p-(methylthio)phenyl group, a pentafluorophenyl group, a benzyl group, a triphenylmethyl group, a diphenylmethyl group, a bis(o-nitrophenyl)methyl group, a 9-anthranylmethyl group, a 2-(9,10-dioxo)anthranylmethyl group, a 5-dibenzosuberyl group, a 1-pyrenylmethyl group, a 2-(trifluoromethyl)-6-chromonylmethyl group, a 2,4,6-trimethylbenzyl group, a p-bromobenzyl group, an o-nitrobenzyl group, a p-nitrobenzyl group, a p-methoxybenzyl group, a 2,6-dimethoxybenzyl group, a 4-(methylsulfinyl)benzyl group, a 4-sulfobenzyl group, a 4-azidomethoxybenzyl group, a piperonyl group, a 4-piconyl group, a trimethylsilyl group, a triethylsilyl group, a tert-butyldimethylsilyl group, an isopropyldimethylsilyl group, a phenyldimethylsilyl group, a di(tert-butyl)methylsilyl group, a triisopropylsilyl group, a $C_1$ to $C_6$ alkylthio group, an oxazole group, a 2-alkyl-1,3-oxazoline group, a 4-alkyl-5-oxyo-1,3-oxazolidine group, a 2,2-bistrifluoromethyl-4-alkyl-5-oxo-1,3-oxazolidine group, a 5-alkyl-4-oxo-1,3-dioxolane group, a dioxanone group, and the like. However, the present invention is not limited to the groups exemplified herein and any group that is capable of being the protecting group for the carboxyl group may be subject to this.

The term "amide-type protecting group for a carboxyl group" in the present invention means a group that protects the carboxyl group by binding with the carbonyl carbon atom of the carboxyl group to be protected and form an amide. Such an "amide-type protecting group for a carboxyl group" includes a protecting group for the carboxyl group described in "Protective Groups in Organic Synthesis (3rd Ed., 1994, 4th Ed., 2006)" by T. W. Greene and P. G. M. Wuts, such as an N,N-dimethylamino group, a pyrrolidinyl group, a piperidinyl group, a 5,6-dihydrophenanthridyl group, an o-nitrophenylamino group, an N-7-nitroindolyl group, an N-8-nitro-1,2,3,4-tetrahydroquinolyl group, an N-phenylhydrazyl group, an N,N'-diisopropylhydrazyl group, and the like. However, the present invention is not limited to those groups exemplified herein and any amino group that is capable of being the protecting group for the carboxyl group may be used for this purpose.

The "protecting group" in the present invention may be supported by a solid material such as resin or silica gel.

The "diazonium group" in the present invention can form a salt. Such a salt includes fluoride, chloride, bromide, iodide, a tetrafluoroborate, and the like.

Abbreviations used in the present invention are as follows:
OTf: a trifluoromethanesulfonyloxy group, OMs: a methansulfonyloxy group,
OTs: a toluenesulfonyloxy group, Me: a methyl group, Et: an ethyl group,
n-Pr: a n-propyl group, i-Pr: an isopropyl group, i-Bu: an isobutyl group,
t-Bu: a tert-butyl group, MeO: a methoxy group, Ph: a phenyl group, OAc: an acetyloxy group, 4-MeO-Ph: a 4-methoxyphenyl group, Cy: a cyclohexyl group, Piv: a pivaloyl group.

The present invention relates to a method of production comprising reacting

Compound 6

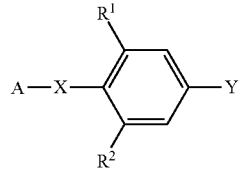

(1)

a compound represented by the above-mentioned formula (1) and a compound represented by the following formula (2), Compound 7

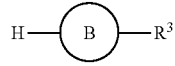

(2)

in the presence of
(i) a palladium compound,
(ii) a ligand capable of coordinating to the palladium compound or a salt thereof,
(iii) a base,
(iv) a $C_1$ to $C_{40}$ carboxylic acid or a salt thereof, and
(v) at least one additive selected from the group consisting of copper, silver, a salt thereof, and a complex thereof, Compound 8

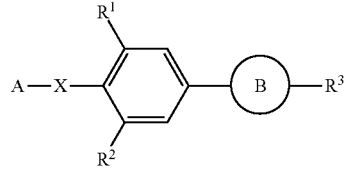

(3)

to produce a phenyl-substituted heterocyclic derivative represented by formula (3).

In the above-mentioned formulae (1) and (3), $R^1$ represents a hydrogen atom or a halogen atom.

The "halogen atom" in $R^1$ is preferably a chlorine atom or a fluorine atom, more preferably a fluorine atom.

As a whole, $R^1$ is preferably a hydrogen atom.

In the above-mentioned formulae (1) and (3), $R^2$ represents a hydrogen atom, a cyano group, a nitro group, a halogen atom, a formyl group, or a halomethyl group.

The "halogen atom" in $R^2$ is preferably a bromine atom.

The "halomethyl group" in $R^2$ is preferably a chloromethyl group, a dichloromethyl group, a trichloromethyl group, or a trifluoromethyl group.

As a whole, $R^2$ is preferably a cyano group, a nitro group, or a formyl group. Above all, a cyano group is preferable.

In the above-mentioned formulae (1) and (3), A represents a hydrogen atom, a $C_1$ to $C_8$ alkyl group, a $C_3$ to $C_6$ cycloalkyl group, a phenyl group, a fluorine atom (only when X is a bond), or a protecting group for a hydroxyl group (only when X is an oxygen atom). Herein, the protecting group for the hydroxyl group as A is employed as the protecting group for the hydroxyl group when X is an oxygen atom. For example, when the protecting group is a benzyl group, A-X- corresponds to $PhCH_2$—O—.

Furthermore, A may be substituted with 1 to 3 substituents, and such a substituent is a group selected from the group consisting of a halogen atom, a $C_1$ to $C_4$ alkyl group, a $C_1$ to $C_4$ alkoxy group, a $C_1$ to $C_4$ alkylthio group, a $C_3$ to $C_6$ cycloalkyl group, a phenyl group, a phenoxy group, and a pyridyl group.

The "$C_1$ to $C_8$ alkyl group" in A is preferably a methyl group, an ethyl group, a n-propyl group, an isopropyl group, a n-butyl group, an isobutyl group, a tert-butyl group, a n-pentyl group, an isopentyl group, or a neopentyl group. Above all, an isobutyl group or a neopentyl group is preferable, and an isobutyl group is more preferable.

As a whole, A is preferably a $C_1$ to $C_5$ alkyl group.

In the above-mentioned formulae (1) and (3), wherein X represents a bond (only when A is a phenyl group or a fluorine atom) or an oxygen atom. Above all, an oxygen atom is preferable.

In the above-mentioned formula (1), Y represents a leaving group. Above all, a halogen atom, —$OCO_2$—($C_1$ to $C_4$ alkyl group), —$OCO_2$—(phenyl group), —$OSO_2$—($C_1$ to $C_4$ alkyl group), —$OSO_2$—(phenyl group), or a diazonium group is preferable.

When the leaving group as Y is "—$OCO_2$—($C_1$ to $C_4$ alkyl group)" or "—$OSO_2$—($C_1$ to $C_4$ alkyl group)", such a "$C_1$ to $C_4$ alkyl group" in Y is preferably a methyl group.

When the leaving group as Y is "—$OCO_2$—($C_1$ to $C_4$ alkyl group)" or "—$OSO_2$—($C_1$ to $C_4$ alkyl group)", such a "$C_1$ to $C_4$ alkyl group" in Y may be substituted with 1 to 3 halogen atoms. Such a "halogen atom" is preferably a fluorine atom, in particular, the group substituted with 3 fluorine atoms is preferable.

When the leaving group as Y is "—$OCO_2$-(phenyl group)" or "—$OSO_2$-(phenyl group)", such a "phenyl group" in Y may be substituted with 1 to 5 optional substituents selected from a halogen atom and a $C_1$ to $C_4$ alkyl group. Such a "$C_1$ to $C_4$ alkyl group" is preferably a methyl group.

When the leaving group as Y is the "halogen atom", such a "halogen atom" is preferably an iodine atom, bromine atom, or chlorine atom. Above all, an iodine atom or a bromine atom is preferable.

The "diazonium group" can form a salt. When the leaving group as Y represents a "diazonium group", a tetrafluoroborate is preferable as the salt of the "diazonium group".

As a whole, Y is preferably an iodine atom, a bromine atom, a trifluoromethanesulfonyloxy group, or the like.

In the above-mentioned formula (2), H represents a hydrogen atom.

In the above-mentioned formulae (2) and (3), B represents a group selected from the following formulae. A bond at the right-hand side of each following formula binds to $R^3$, a bond at the left-hand side binds to a hydrogen atom in formula (2) and to a phenyl group in formula (3).

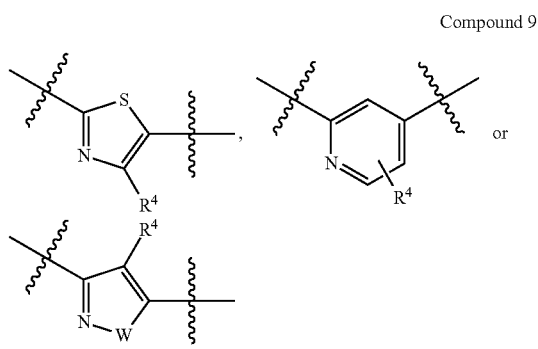

Compound 9

Above all, the following groups are preferable.

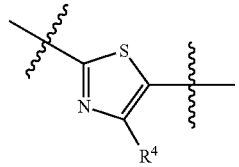

Compound 10

In the above-mentioned formulae (2) and (3), $R^3$ represents $COOR^{3a}$ or $COR^{3b}$.

$R^{3a}$ represents a hydrogen atom, a $C_1$ to $C_4$ alkyl group, or an ester-type protecting group for a carboxyl group. Herein, the ester-type protecting group for the carboxyl group as $R^{3a}$ protects a carboxyl group to be substituted with $R^{3a}$.

$R^{3a}$ is preferably a hydrogen atom or a $C_1$ to $C_4$ alkyl group, and more preferably a $C_1$ to $C_4$ alkyl group.

$R^{3b}$ represents an amide-type protecting group for a carboxyl group that forms an amide with an adjacent carbonyl group.

As a whole, $R^3$ is preferably $COOR^{3a}$ and $R^{3a}$ is preferably a $C_1$ to $C_4$ alkyl group.

In B of the above-mentioned formulae (2) and (3), $R^4$ represents a hydrogen atom, a halogen atom, or a $C_1$ to $C_4$ alkyl group.

The "halogen atom" in $R^4$ is preferably a fluorine atom.

The "$C_1$ to $C_4$ alkyl group" in $R^4$ is preferably a methyl group.

As a whole, $R^4$ is preferably a $C_1$ to $C_4$ alkyl group. Above all, a methyl group is preferable.

In B of the above-mentioned formulae (2) and (3), W represents an oxygen atom or a sulfur atom.

In the above-mentioned formula (3), the definition of A, X, $R^1$, $R^2$ and a preferable group are the same as those defined in formula (1), the definition of B and $R^3$, and a preferable group are the same as those defined in formula (2), respectively.

Specific examples of the compound represented by formula (1) are listed in Table 1 to 4 and specific examples of the compound represented by formula (2) are listed in Tables 5 to 7. However, the compounds represented by formulae (1) and (2) are not limited to such specific examples.

TABLE 1

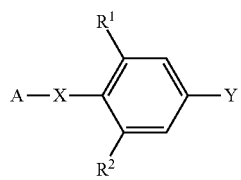

(1)

| No. | A | X | R¹ | R² | Y |
|---|---|---|---|---|---|
| 1 | i-Bu | O | H | CN | I |
| 2 | i-Bu | O | H | CN | Br |
| 3 | i-Bu | O | H | CN | Cl |
| 4 | i-Bu | O | H | CN | OTf |
| 5 | i-Bu | O | H | CN | OMs |
| 6 | i-Bu | O | H | CN | OTs |
| 7 | i-Bu | O | H | CHO | I |
| 8 | i-Bu | O | H | CHO | Br |
| 9 | i-Bu | O | H | CHO | Cl |
| 10 | i-Bu | O | H | CHO | OTf |
| 11 | i-Bu | O | H | CHO | OMs |
| 12 | i-Bu | O | H | CHO | OTs |
| 13 | i-Bu | O | H | NO₂ | I |
| 14 | i-Bu | O | H | NO₂ | Br |
| 15 | i-Bu | O | H | NO₂ | Cl |
| 16 | i-Bu | O | H | NO₂ | OTf |
| 17 | i-Bu | O | H | NO₂ | OMs |
| 18 | i-Bu | O | H | NO₂ | OTs |
| 19 | i-Bu | O | H | H | I |
| 20 | i-Bu | O | H | H | Br |
| 21 | i-Bu | O | H | H | Cl |
| 22 | i-Bu | O | H | H | OTf |
| 23 | i-Bu | O | H | H | OMs |
| 24 | i-Bu | O | H | H | OTs |
| 25 | i-Bu | O | H | Br | I |
| 26 | i--Bu | O | H | Br | Br |
| 27 | i-Bu | O | H | Br | Cl |
| 28 | i-Bu | O | H | Br | OTf |
| 29 | i-Bu | O | H | Br | OMs |
| 30 | i-Bu | O | H | Br | OTs |
| 31 | (CH₃)₃CCH₂ | O | H | CN | I |
| 32 | (CH₃)₃CCH₂ | O | H | CN | Br |
| 33 | (CH₃)₃CCH₂ | O | H | CN | Cl |
| 34 | (CH₃)₃CCH₂ | O | H | CN | OTf |
| 35 | (CH₃)₃CCH₂ | O | H | CN | OMs |
| 36 | (CH₃)₃CCH₂ | O | H | CN | OTs |
| 37 | (CH₃)₃CCH₂ | O | H | CHO | I |
| 38 | (CH₃)₃CCH₂ | O | H | CHO | Br |
| 39 | (CH₃)₃CCH₂ | O | H | CHO | Cl |
| 40 | (CH₃)₃CCH₂ | O | H | CHO | OTf |
| 41 | (CH₃)₃CCH₂ | O | H | CHO | OMs |
| 42 | (CH₃)₃CCH₂ | O | H | CHO | OTs |

TABLE 2

| No. | A | X | R¹ | R² | Y |
|---|---|---|---|---|---|
| 43 | (CH₃)₃CCH₂ | O | H | NO₂ | I |
| 44 | (CH₃)₃CCH₂ | O | H | NO₂ | Br |
| 45 | (CH₃)₃CCH₂ | O | H | NO₂ | Cl |
| 46 | (CH₃)₃CCH₂ | O | H | NO₂ | OTf |
| 47 | (CH₃)₃CCH₂ | O | H | NO₂ | OMs |
| 48 | (CH₃)₃CCH₂ | O | H | NO₂ | OTs |
| 49 | (CH₃)₃CCH₂ | O | H | H | I |
| 50 | (CH₃)₃CCH₂ | O | H | H | Br |
| 51 | (CH₃)₃CCH₂ | O | H | H | Cl |
| 52 | (CH₃)₃CCH₂ | O | H | H | OTf |
| 53 | (CH₃)₃CCH₂ | O | H | H | OMs |

TABLE 2-continued

| No. | A | X | R¹ | R² | Y |
|---|---|---|---|---|---|
| 54 | (CH₃)₃CCH₂ | O | H | H | OTs |
| 55 | (CH₃)₃CCH₂ | O | H | Br | I |
| 56 | (CH₃)₃CCH₂ | O | H | Br | Br |
| 57 | (CH₃)₃CCH₂ | O | H | Br | Cl |
| 58 | (CH₃)₃CCH₂ | O | H | Br | OTf |
| 59 | (CH₃)₃CCH₂ | O | H | Br | OMs |
| 60 | (CH₃)₃CCH₂ | O | H | Br | OTs |
| 61 | Benzyl | O | H | CN | I |
| 62 | Benzyl | O | H | CN | Br |
| 63 | Benzyl | O | H | CN | Cl |
| 64 | Benzyl | O | H | ON | OTf |
| 65 | Benzyl | O | H | CN | OMs |
| 66 | Benzyl | O | H | CN | OTs |
| 67 | Benzyl | O | H | CHO | I |
| 68 | Benzyl | O | H | CHO | Br |
| 69 | Benzyl | O | H | CHO | Cl |
| 70 | Benzyl | O | H | CHO | OTf |
| 71 | Benzyl | O | H | CHO | OMs |
| 72 | Benzyl | O | H | CHO | OTs |
| 73 | Benzyl | O | H | NO₂ | I |
| 74 | Benzyl | O | H | NO₂ | Br |
| 75 | Benzyl | O | H | NO₂ | Cl |
| 76 | Benzyl | O | H | NO₂ | OTf |
| 77 | Benzyl | O | H | NO₂ | OMs |
| 78 | Benzyl | O | H | NO₂ | OTs |
| 79 | Benzyl | O | H | H | I |
| 80 | Benzyl | O | H | H | Br |
| 81 | Benzyl | O | H | H | Cl |
| 82 | Benzyl | O | H | H | OTf |
| 83 | Benzyl | O | H | H | OMs |
| 84 | Benzyl | O | H | H | OTs |

TABLE 3

| No. | A | X | R¹ | R² | Y |
|---|---|---|---|---|---|
| 85 | Benzyl | O | H | Br | I |
| 86 | Benzyl | O | H | Br | Br |
| 87 | Benzyl | O | H | Br | Cl |
| 88 | Benzyl | O | H | Br | OTf |
| 89 | Benzyl | O | H | Br | OMs |
| 90 | Benzyl | O | H | Br | OTs |
| 91 | Ph | bond | H | CN | I |
| 92 | Ph | bond | H | CN | Br |
| 93 | Ph | bond | H | CN | Cl |
| 94 | Ph | bond | H | CN | OTf |
| 95 | Ph | bond | H | CN | OMs |
| 96 | Ph | bond | H | CN | OTs |
| 97 | Ph | bond | H | CHO | I |
| 98 | Ph | bond | H | CHO | Br |
| 99 | Ph | bond | H | CHO | Cl |
| 100 | Ph | bond | H | CHO | OTf |
| 101 | Ph | bond | H | CHO | OMs |
| 102 | Ph | bond | H | CHO | OTs |
| 103 | Ph | bond | H | NO₂ | I |
| 104 | Ph | bond | H | NO₂ | Br |
| 105 | Ph | bond | H | NO₂ | Cl |
| 106 | Ph | bond | H | NO₂ | OTf |
| 107 | Ph | bond | H | NO₂ | OMs |
| 108 | Ph | bond | H | NO₂ | OTs |
| 109 | Ph | bond | H | H | I |
| 110 | Ph | bond | H | H | Br |
| 111 | Ph | bond | H | H | Cl |
| 112 | Ph | bond | H | H | OTf |
| 113 | Ph | bond | H | H | OMs |
| 114 | Ph | bond | H | H | OTs |
| 115 | Ph | bond | H | Br | I |
| 116 | Ph | bond | H | Br | Br |
| 117 | Ph | bond | H | Br | Cl |
| 118 | Ph | bond | H | Br | OTf |
| 119 | Ph | bond | H | Br | OMs |
| 120 | Ph | bond | H | Br | OTs |
| 121 | 4-MeO—Ph | bond | H | CN | I |
| 122 | 4-MeO—Ph | bond | H | CN | Br |
| 123 | 4-MeO—Ph | bond | H | CN | Cl |

TABLE 3-continued

| No. | A | X | R¹ | R² | Y |
|---|---|---|---|---|---|
| 124 | 4-MeO—Ph | bond | H | CN | OTf |
| 125 | 4-MeO—Ph | bond | H | CN | OMs |
| 126 | 4-MeO—Ph | bond | H | CN | OTs |

TABLE 4

| No. | A | X | R¹ | R² | Y |
|---|---|---|---|---|---|
| 127 | 4-MeO—Ph | bond | H | CHO | I |
| 128 | 4-MeO—Ph | bond | H | CHO | Br |
| 129 | 4-MeO—Ph | bond | H | CHO | Cl |
| 130 | 4-MeO—Ph | bond | H | CHO | OTf |
| 131 | 4-MeO—Ph | bond | H | CHO | OMs |
| 132 | 4-MeO—Ph | bond | H | CHO | OTs |
| 133 | 4-MeO—Ph | bond | H | $NO_2$ | I |
| 134 | 4-MeO—Ph | bond | H | $NO_2$ | Br |
| 135 | 4-MeO—Ph | bond | H | $NO_2$ | Cl |
| 136 | 4-MeO—Ph | bond | H | $NO_2$ | OTf |
| 137 | 4-MeO—Ph | bond | H | $NO_2$ | OMs |
| 138 | 4-MeO—Ph | bond | H | $NO_2$ | OTs |
| 139 | 4-MeO—Ph | bond | H | H | I |
| 140 | 4-MeO—Ph | bond | H | H | Br |
| 141 | 4-MeO—Ph | bond | H | H | Cl |
| 142 | 4-MeO—Ph | bond | H | H | OTf |
| 143 | 4-MeO—Ph | bond | H | H | OMs |
| 144 | 4-MeO—Ph | bond | H | H | OTs |
| 145 | 4-MeO—Ph | bond | H | Br | I |
| 146 | 4-MeO—Ph | bond | H | Br | Br |
| 147 | 4-MeO—Ph | bond | H | Br | Cl |
| 148 | 4-MeO—Ph | bond | H | Br | OTf |
| 149 | 4-MeO—Ph | bond | H | Br | OMs |
| 150 | 4-MeO—Ph | bond | H | Br | OTs |

TABLE 5

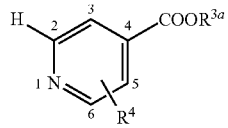

| No. | $R^{3a}$ | $R^4$ |
|---|---|---|
| 151 | t-Bu | $CH_3$ |
| 152 | n-Pr | $CH_3$ |
| 153 | i-Pr | $CH_3$ |
| 154 | Et | $CH_3$ |
| 155 | Me | $CH_3$ |
| 156 | H | $CH_3$ |
| 157 | t-Bu | H |
| 158 | n-Pr | H |
| 159 | i-Pr | H |
| 160 | Et | H |
| 161 | Me | H |
| 162 | H | H |

TABLE 6

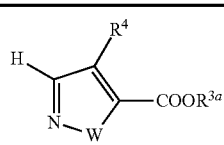

| No. | $R^{3a}$ | $R^4$ |
|---|---|---|
| 163 | t-Bu | 5-$CH_3$ |
| 164 | n-Pr | 5-$CH_3$ |
| 165 | i-Pr | 5-$CH_3$ |

TABLE 6-continued

| No. | $R^{3a}$ | $R^4$ |
|---|---|---|
| 166 | Et | 5-$CH_3$ |
| 167 | Me | 5-$CH_3$ |
| 168 | H | 5-$CH_3$ |
| 169 | t-Bu | H |
| 170 | n-Pr | H |
| 171 | i-Pr | H |
| 172 | Et | H |
| 173 | Me | H |
| 174 | H | H |
| 175 | t-Bu | 3-F |
| 176 | n-Pr | 3-F |
| 177 | i-Pr | 3-F |
| 178 | Et | 3-F |
| 179 | Me | 3-F |
| 180 | H | 3-F |
| 181 | t-Bu | 5-Cl |
| 182 | n-Pr | 5-Cl |
| 183 | i-Pr | 5-Cl |
| 184 | Et | 5-Cl |
| 185 | Me | 5-Cl |
| 186 | H | 5-Cl |

TABLE 7

| No. | W | $R^{3a}$ | $R^4$ |
|---|---|---|---|
| 187 | O | t-Bu | $CH_3$ |
| 188 | O | n-Pr | $CH_3$ |
| 189 | O | i-Pr | $CH_3$ |
| 190 | O | Et | $CH^3$ |
| 191 | O | Me | $CH_3$ |
| 192 | O | H | $CH_3$ |
| 193 | O | t-Bu | H |
| 194 | O | n-Pr | H |
| 195 | O | i-Pr | H |
| 196 | O | Et | H |
| 197 | O | Me | H |
| 198 | O | H | H |
| 199 | S | t-Bu | $CH_3$ |
| 200 | S | n-Pr | $CH_3$ |
| 201 | S | i-Pr | $CH_3$ |
| 202 | S | Et | $CH_3$ |
| 203 | S | Me | $CH_3$ |
| 204 | S | H | $CH_3$ |
| 205 | S | t-Bu | H |
| 206 | S | n-Pr | H |
| 207 | S | i-Pr | H |
| 208 | S | Et | H |
| 209 | S | Me | H |
| 210 | S | H | H |

The method of production in the present invention is characterized by reacting using
(i) a palladium compound,
(ii) a ligand capable of coordinating to the palladium compound or a salt thereof,
(iii) a base,
(iv) a $C_1$ to $C_{40}$ carboxylic acid or a salt thereof, and
(v) at least one additive selected from the group consisting of copper, silver, and a salt thereof and a complex thereof.

[A Palladium Compound]

The palladium compound used in the present invention is preferably zerovalent palladium, or a salt of monovalent or divalent palladium.

The salts of monovalent palladium include, for example, dibromo-dipalladium (I), hydrates thereof, and the like.

The salts of divalent palladium include, for example, palladium(II) acetate, palladium(II) propionate, palladium(II) butanoate, palladium(II) 2-methylpropanoate, palladium(II) 3-methylbutanoate, palladium(II) 2-methylbutanoate, palladium(II) 2-ethylbutanoate, palladium(II) pivalate, palladium (II) 3,3-dimethylbutanoate, palladium(II) 2,2,3,3-tetramethylbutanoate, palladium(II) 1-adamantanecarboxylate, palladium(II) 2-adamantanecarboxylate, palladium(II) 3-noradamantanecarboxylate, palladium(II) trifluoroacetate, palladium(II) nitrate, palladium(II) chloride, palladium(II) bromide, palladium(II) iodide, palladium(II) acetylacetonate, palladium(II) perchlorate, palladium(II) citrate, palladium (II) oxalate, palladium(II) cyclohexanebutyrate, palladium (II) benzoate, palladium(II) stearate, palladium(II) sulfamate, palladium(II) carbonate, palladium(II) thiocyanate, palladium(II) trifluoromethanesulfonate, bis(4-diethylaminodithiobenzyl)palladium(II), palladium(II) cyanide, palladium(II) fluoride, palladium(II) boride, palladium(II) borate, palladium(II) hypophosphite, palladium(II) ammonium sulfate, palladium(II) hydroxide, cyclopentadienyl palladium (II), hydrates thereof, and the like.

Above all, palladium(II) acetate (Pd(OAc)$_2$), palladium(II) propionate (Pd(O(C=O)CH$_2$CH$_3$)$_2$), palladium(II) 2-methylpropanoate (Pd(O(C=O)CH(CH$_3$)$_2$)$_2$), palladium(II) pivalate (Pd(OPiv)$_2$), palladium(II) 1-adamantanecarboxylate, palladium(II) chloride (PdCl$_2$), palladium(I) bromide (Pd$_2$Br$_2$), palladium(II) bromide (PdBr$_2$), or palladium(0) is preferable, in particular, palladium(II) 2-methylpropanoate (Pd(O(C=O)CH(CH$_3$)$_2$)$_2$), palladium(II) pivalate (Pd (OPiv)$_2$), palladium(II) bromide (PdBr$_2$), palladium(II) chloride (PdCl$_2$), or palladium(0) is preferable.

These palladium compounds may be used in mixed combination.

As these palladium compounds, a compound coordinated by a ligand in advance may be employed. Such a palladium compound coordinated by the ligand includes, for example, the following palladium compounds. However, the present invention is not limited to these.

Compound 11

Pd(P$^t$Bu$_3$)$_2$

[Pd(P$^t$Bu$_3$)Br]$_2$

PdCl$_2$($^t$Bu$_2$Ph)$_2$

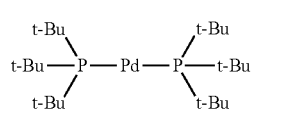

Pd(P$^t$Bu$_2$Cy)$_2$

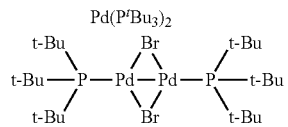

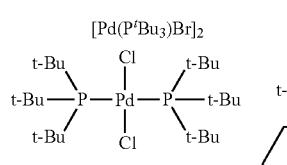

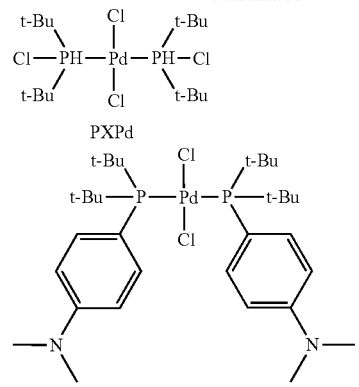

PXPd

PdCl$_2$[(P$^t$Bu$_2$(p-NMe$_2$Ph)]$_2$

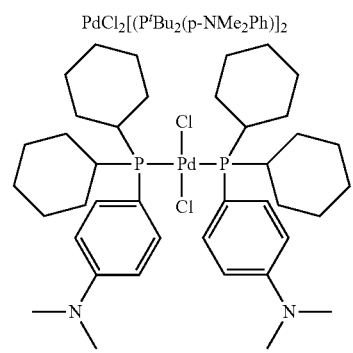

PdCl$_2$[(PCy$_2$(p-NMe$_2$Ph)]$_2$

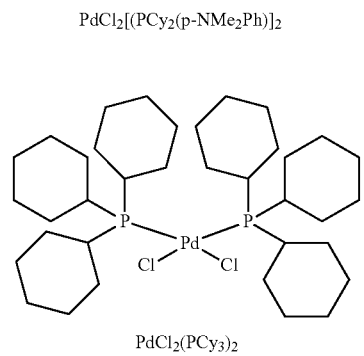

PdCl$_2$(PCy$_3$)$_2$

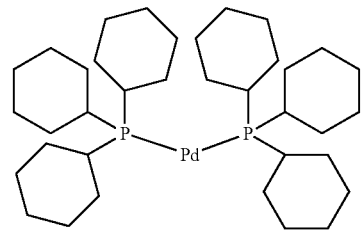

Pd(PCy$_3$)$_2$

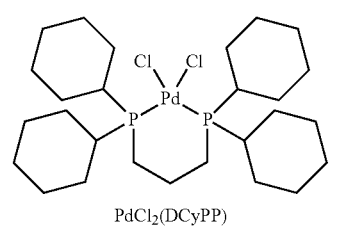

PdCl$_2$(DCyPP)

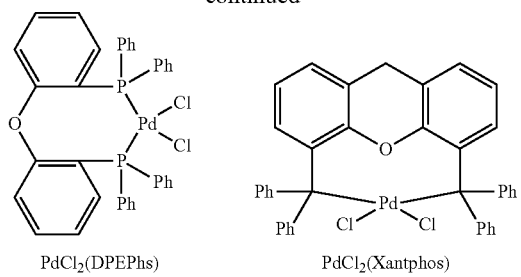

PdCl₂(DPEPhs)

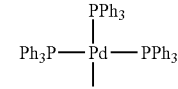

PdCl₂(Xantphos)

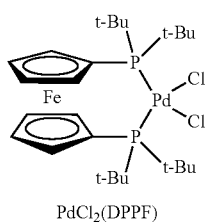

PdCl₂(DPPF)

Ph₃P—Pd—PPh₃ with PPh₃ (top) and PPh₃ (bottom)

Pd(PPh₃)₄

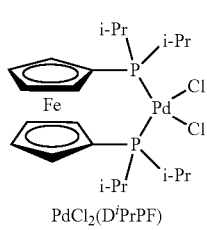

PdCl₂(D^iPrPF)

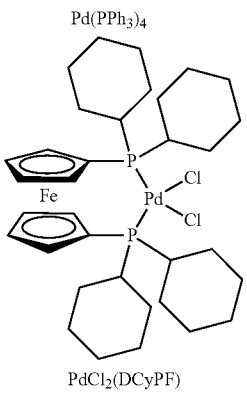

PdCl₂(DCyPF)

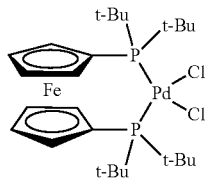

PdCl₂(D^tBuPF)

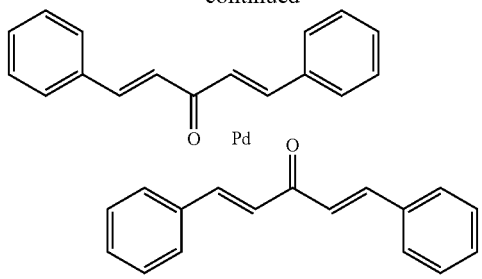

Pd(dba)₂

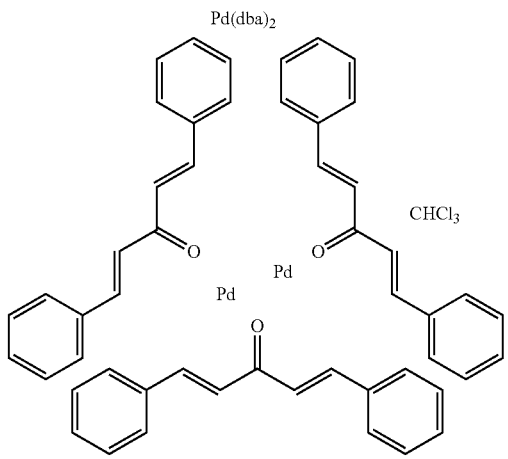

Pd₂(dba)₃·CHCl₃

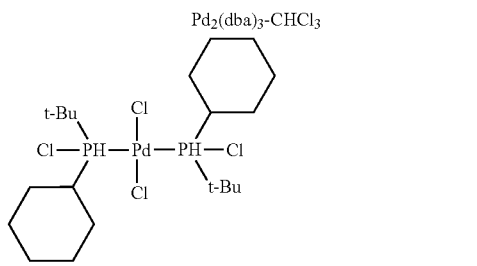

PXPd3

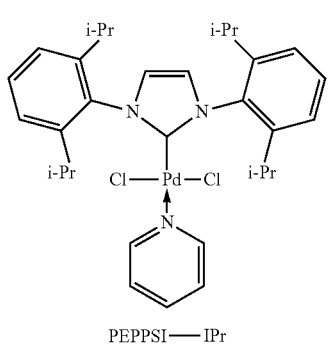

PEPPSI—IPr

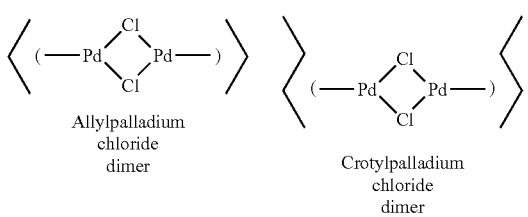

Allylpalladium chloride dimer

Crotylpalladium chloride dimer

[A Ligand Capable of Coordinating to a Palladium Compound and a Salt Thereof]

The presence of a ligand that is capable of coordinating to the palladium compound in the course of the reaction facilitates coupling of a phenyl ring of a phenyl derivative to a heterocyclic derivative at the position of C—H bond on the heterocyclic ring with good substrate selectivity and thus, the yield of the compound represented by formula (3) can be increased. Such a ligand used in the production method of the present invention includes a ligand of carboxylic acid-type, amide-type, phosphine-type, oxime-type, sulfide-type, sulfonic acid-type, 1,3-diketone-type, Shiff base-type, oxazoline-type, diamine-type, hydrocarbon-type, carbon monoxide, carbene-type, and the like. However, the present invention is not limited to these. The coordinating atom in the ligand includes a nitrogen atom, a phosphorus atom, an oxygen atom, a sulfur atom, and the like. There are a monodentate ligand having one coordinating atom at only one position and a multidentate ligand having coordinating atoms at two or more positions. A hydrocarbon-type, carbon monoxide and carbene-type have a carbon atom as the coordinating atom. These ligands may be used as salts.

The monodentate ligand includes a phosphine-type ligand represented by $R^5P(R^6)R^7$ (wherein $R^5$, $R^6$, and $R^7$ represent each independently a $C_1$ to $C_8$ alkyl group, a $C_1$ to $C_4$ alkoxy group, an alicyclic hydrocarbon group, a $C_6$ to $C_{12}$ aryl group, a heteroaryl group, a $C_6$ to $C_{12}$ aryloxy group, or a heteroaryloxy group. In addition, $R^5$ and $R^6$ may bind together to form $C_2$ to $C_8$ alkylene group), triethylamine, heteroarene, and the like.

The phosphine-type ligand represented by $R^5P(R^6)R^7$ includes, for example, tert-butyldicyclohexylphosphine, isobutyldicyclohexylphosphine, (n-butyl)dicyclohexylphosphine, isopropyldicyclohexylphosphine, (n-propyl)dicyclohexylphosphine, ethyldicyclohexylphosphine, methyldicyclohexylphosphine, cyclopropyldicyclohexylphosphine, cyclobutyldicyclohexylphosphine, tert-butyldicyclooctylphosphine, tert-butyldicycloheptylphosphine, tert-butyldicyclopentylphosphine, tert-butyldicyclobutylphosphine, tert-butyldicyclopropylphosphine, triethylphosphine, tri(n-propyl)phosphine, tri(isopropyl)phosphine, tri(tert-butyl)phosphine, tri(n-butyl)phosphine, tri(n-octyl)phosphine, tri(cyclooctyl)phosphine, tri(cycloheptyl)phosphine, tri(cyclohexyl)phosphine, tri(cyclopentyl)phosphine, tri(cyclobutyl)phosphine, tri(cyclopropyl)phosphine, di(tert-butyl)methylphosphine, di(tert-butyl)ethylphosphine, di(tert-butyl)n-propylphosphine, di(tert-butyl)isopropylphosphine, di(tert-butyl)n-butylphosphine, di(tert-butyl)isobutylphosphine, di(tert-butyl)neopentylphosphine, triphenylphosphine, tri(o-toluoyl)phosphine, tri(mesityl)phosphine, tri(phenoxy)phosphine, tri(2-furyl)phosphine, trimethoxyphosphine, triethoxyphosphine, tri(n-propyloxy)phosphine, tri(isopropyloxy)phosphine, tri(n-butyloxy)phosphine, tri(isobutyloxy)phosphine, tri(tert-butyloxy)phosphine, di(tert-butyl)cyclohexylphosphine, di(isobutyl)cyclohexylphosphine, di(n-butyl)cyclohexylphosphine, di(isopropyl)cyclohexylphosphine, di(n-propyl)cyclohexylphosphine, diethylcyclohexylphosphine, dimethylcyclohexylphosphine, di(tert-butyl)cyclopentylphosphine, di(isobutyl)cyclopentylphosphine, di(n-butyl)cyclopentylphosphine, di(isopropyl)cyclopentylphosphine, di(n-propyl)cyclopentylphosphine, diethylcyclopentylphosphine, dimethylcyclopentylphosphine, di(tert-butyl)cyclooctylphosphine, di(tert-butyl)cycloheptylphosphine, di(tert-butyl)cyclopentylphosphine, di(tert-butyl)cyclobutylphosphine, di(tert-butyl)cyclopropylphosphine, dimethylphenylphosphine, diethylphenylphosphine, di(n-propyl)phenylphosphine, di(isopropyl)phenylphosphine, di(n-butyl)phenylphosphine, di(isobutyl)phenylphosphine, di(tert-butyl)phenylphosphine, dicyclooctylphenylphosphine, dicycloheptylphenylphosphine, dicyclohexylphenylphosphine, dicyclopentylphenylphosphine, dicyclobutylphenylphosphine, dicyclopropylphenylphosphine, dicyclohexyl-(p-toluyl)phosphine, dicyclohexyl-(o-toluyl)phosphine, dicyclohexyl-(p-toluyl)phosphine, dicyclohexyl-(2,4,6-trimethylphenyl)phosphine, methyldiphenylphosphine, ethyldiphenylphosphine, (n-propyl)diphenylphosphine, isopropyldiphenylphosphine, (n-butyl)diphenylphosphine, isobutyldiphenylphosphine, (tert-butyl)diphenylphosphine, cyclooctyldiphenylphosphine, cycloheptyldiphenylphosphine, cyclohexyldiphenylphosphine, cyclopentyldiphenylphosphine, cyclobutyldiphenylphosphine, cyclopropyldiphenylphosphine, bis(p-sulfonatophenyl)phenylphosphine potassium, 2-(2'-dicyclohexylphosphinophenyl)-1,3-dioxolane, cBRIDP, XPhos(2-dicyclohexylphosphino-2',4',6'-triisopropyl-1,1'-biphenyl), t-Bu-XPhos, JohnPhos, Cy-JohnPhos, MePhos, t-Bu-MePhos, SPhos, RuPhos(2-dicyclohexylphosphino-2',6'-diisopropoxy-1,1'-biphenyl), cataCXium A, cataCXium ABn, cataCXium PtB, cataCXium PCy, cataCXium POMetB, cataCXium POMeCy, cataCXium PIntB, cataCXium PInCy, cataCXium PICy, Q-Phos, JOSIPHOS, and the like.

Among the examples of the phosphine-type ligand represented by $R^5P(R^6)R^7$ as noted above, the chemical structures of a part of the examples indicated as abbreviations are shown hereinafter.

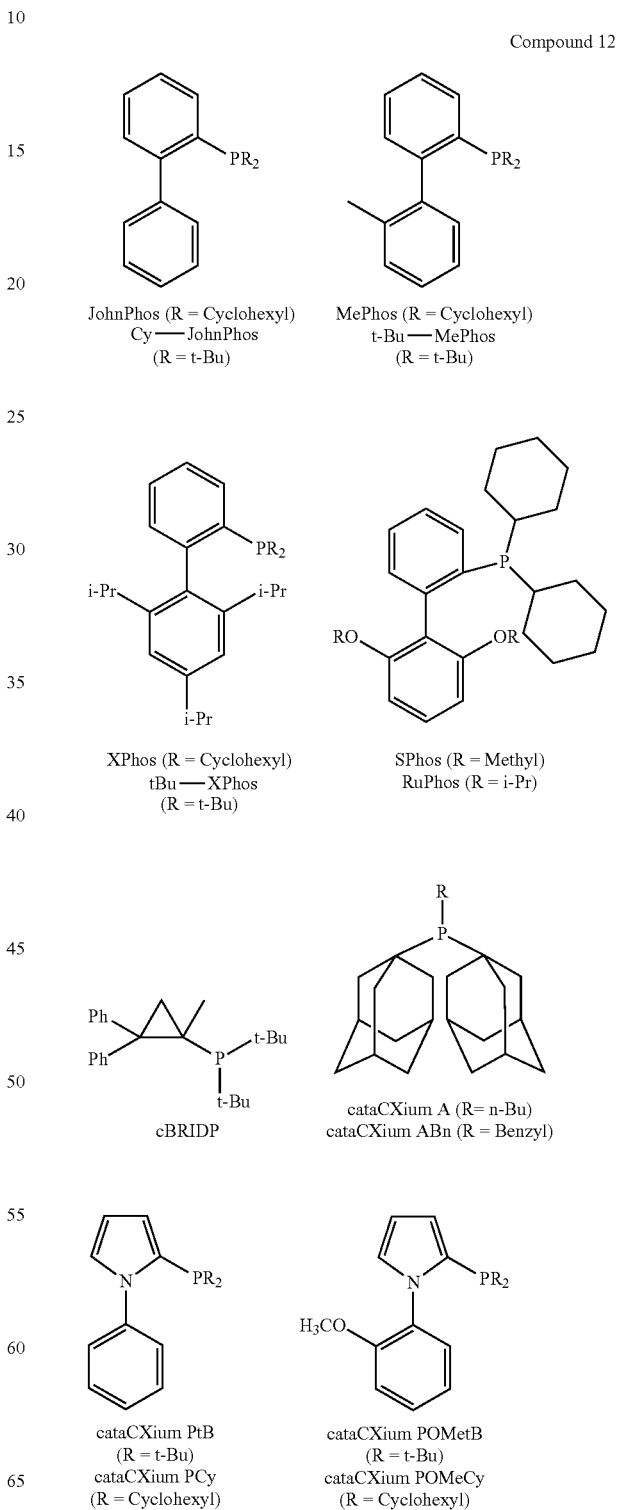

Compound 12

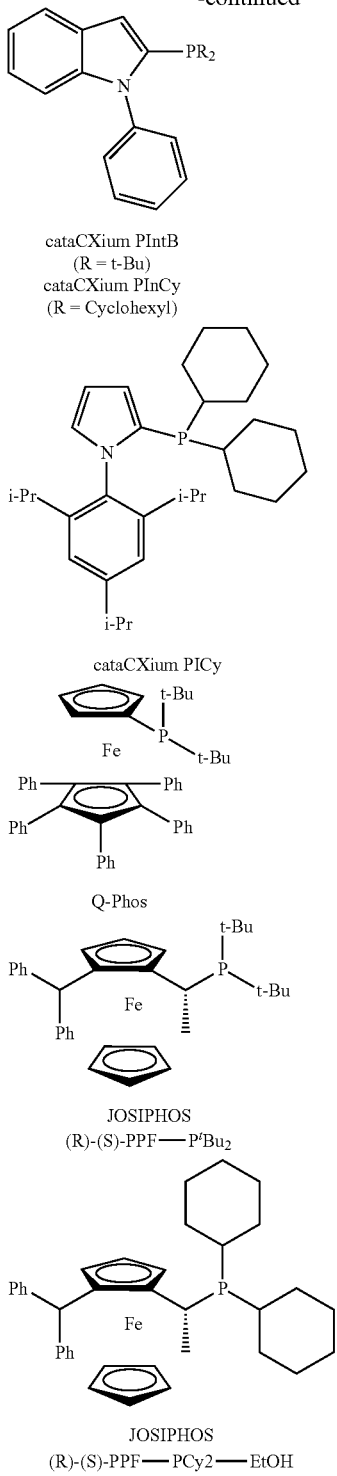

cataCXium PIntB
(R = t-Bu)
cataCXium PInCy
(R = Cyclohexyl)

cataCXium PICy

Q-Phos

JOSIPHOS
(R)-(S)-PPF—P'Bu₂

JOSIPHOS
(R)-(S)-PPF—PCy2—EtOH

The bidentate ligand includes a phosphine-type ligand represented by $R^8(R^9)PR^{10}P(R^{11})R^{12}$, an amine-phosphine-type ligand represented by $R^8(R^9)PR^{10}N(R^{11})R^{12}$, an amine-type ligand represented by $R^8(R^9)NR^{10}N(R^{11})R^{12}$ (wherein $R^8$, $R^9$, $R^{11}$, and $R^{12}$ each independently represent a $C_1$ to $C_8$ alkyl group, a $C_1$ to $C_4$ alkoxy group, an alicyclic hydrocarbon group, a $C_6$ to $C_{12}$ aryl group, a heteroaryl group, a $C_6$ to $C_{12}$ aryloxyl group, or a heteroaryloxy group. $R^{10}$ represents a $C_1$ to $C_8$ alkylene group, a divalent alicyclic hydrocarbon group, a $C_6$ to $C_{12}$ arylene group, or a heteroarylene group. Furthermore, when $R^{11}$ and $R^{12}$ bind to a nitrogen atom, the nitrogen atom bonded to $R^{11}$ and $R^{12}$, $R^{11}$, and $R^{12}$ may form a heteroaryl group together), heteroarene, 1,5-cyclooctadiene, 2-(dimethylamino)ethanol, and the like. Moreover, as the amine-type ligand, examples of the heteroaryl group that can be formed by the nitrogen atom bonded to $R^{11}$ and $R^{12}$, $R^{11}$, and $R^{12}$ together include a pyrrolyl group, an isoxazolyl group, an isothiazolyl group, a pyrazolyl group, an oxazolyl group, an imidazolyl group, a triazolyl group, a tetrazolyl group, a pyridyl group, a pyrimidyl group, a pyridazyl group, a pyrazyl group, a thiazolyl, and the like.

The phosphine-type ligand represented by $R^8(R^9)PR^{10}P(R^{11})R^{12}$ includes, for example, 1-1'-bis(diphenylphosphino)ferrocene, 1,1'-bis(tert-butyl)ferrocene, diphenylphosphinomethane, 1,2-bis(diphenylphosphino)ethane, 1,3-bis(diphenylphosphino)propane, 1,5-bis(diphenylphosphino)pentane, 1,2-bis(dipentafluorophenylphosphino)ethane, 1,2-bis(dicyclohexylphosphino)ethane, 1,3-(dicyclohexylphosphino)propane, 1,4-bis(dicyclohexylphosphino)butane, 1,2-bis(di-tert-butylphosphino)ethane, 1,3-bis(di-tert-butylphosphino)propane, 1,4-bis(di-tert-butylphosphino)butane, 1,2-bis(diphenylphosphino)benzene, BINAP, BIPHEMP, PROPHOS, DIOP, DEGUPHOS, DIPAMP, DuPHOS, NORPHOS, PNNP, SKEWPHOS, BPPFA, SEGPHOS, CHIRAPHOS, DPEphos, Xantphos, and the like.

The amine-phosphine-type ligand represented by $R^8(R^9)PR^{10}N(R^{11})R^{12}$ includes, for example, 2-di(tert-butyl)phosphino-2'-(N,N-dimethylamino)biphenyl, DavePhos, t-Bu-DavePhos, TrippyPhos, BippyPhos, and the like.

The amine-type ligand represented by $R^8(R^9)NR^{10}N(R^{11})R^{12}$ includes, for example, 1,4-diazabicyclo[2,2,2]octane, tetramethylethylenediamine, N,N-dimethylethylenediamine, N,N'-dimethylethylenediamine, 2-aminomethylpyridine, (NE)-N-(pyridin-2-ylmethylidene)aniline, and the like.

Heteroarenes include, for example, 2,2'-bipyridyl, 4,4'-(tert-butyl)bipyridyl, phenanthro line, 2,2'-bipyrimidyl, and the like.

Among the examples of the phosphine-type ligand represented by $R^8(R^9)PR^{10}P(R^{11})R^{12}$ as noted above, the chemical structures of a part of the examples described as abbreviations are shown below:

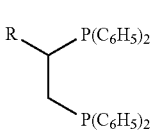

Compound 13

PROPHOS
PROPHOS (R = CH₃)
BENZPHOS (R = C₆H₅CH₂)
CyCPHOS (R = C₆H₁₁)

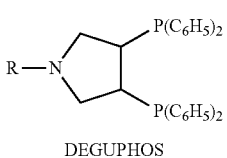

DEGUPHOS

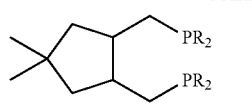
DIOP
DIOP (R = C₆H₅)
CyDIOP (R = C₆H₁₁)
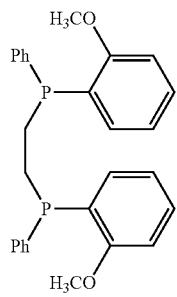
DIPAMP
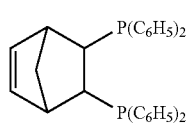
NORPHOS
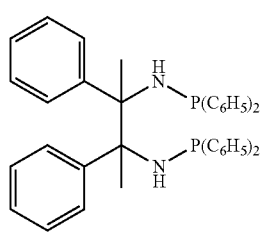
PNNP
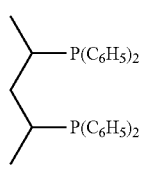
SKEWPHOS
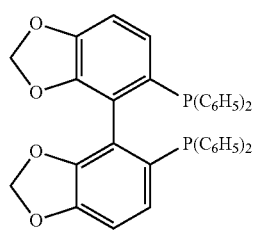
SEGPHOS
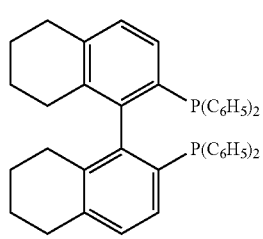
H₈-BINAP
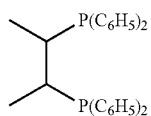
CHIRAPHOS
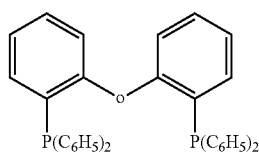
DPEphos
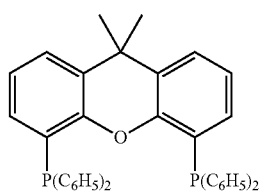
Xantphos
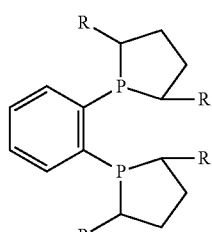
DuPHOS
Me-DuPHOS (R = CH₃)
Et-DuPHOS (R = C₂H₅)
i-Pr-DuPHOS (R = i-Pr)
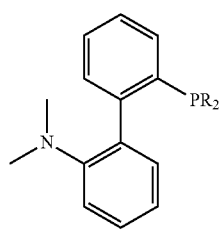
DavePhos (R = Cyclohexyl)
t-Bu-MePhos (R = t-Bu)
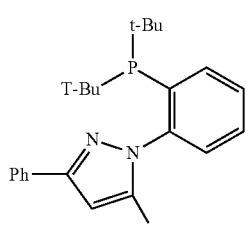
TrippyPhos

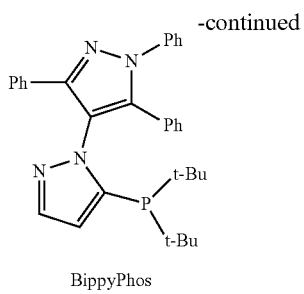

BippyPhos

Derivatives of BINAP are also included as BINAP, and the specific examples include
2,2'-bis(diphenylphosphino)-1,1'-binaphthyl,
2,2'-bis(di-p-tolylphosphino)-1,1'-binaphthyl,
2,2'-bis(di-p-tert-butylphenylphosphino)-1,1'-binaphthyl,
2,2'-bis(di-m-tolylphosphino)-1,1'-binaphthyl,
2,2'-bis(di-3,5-dimethylphenylphosphino)-1,1'-binaphthyl,
2,2'-bis(di-p-methoxyphenylphosphino)-1,1'-binaphthyl,
2,2'-bis(dicyclopentylphosphino)-1,1'-binaphthyl,
2,2'-bis(dicyclohexylphosphino)-1,1'-binaphthyl,
2-di(β-naphthyl)phosphino-2'-diphenylphosphino-1,1'-binaphthyl,
2-diphenylphosphino-2'-di(p-trifluoromethylphenyl)phosphino-1,1'-binaphthyl, and the like.

Derivatives of BIPHEMP are also included as BIPHEMP, and the specific examples include 2,2'-dimethyl-6,6'-bis(diphenylphosphino)-1,1'-biphenyl, 2,2'-dimethyl-6,6'-bis(dicyclohexylphosphino)-1,1'-biphenyl, 2,2'-dimethyl-4,4'-bis(dimethylamino)-6,6'-bis(diphenylphosphino)-1,1'-biphenyl, 2,2',4,4'-tetramethyl-6,6'-bis(diphenylphosphino)-1,1'-biphenyl, 2,2'-dimethoxy-6,6'-bis(diphenylphosphino)-1,1'-biphenyl, 2,2',3,3'-tetramethoxy-6,6'-bis(diphenylphosphino)-1,1'-biphenyl, 2,2',4,4'-tetramethyl-3,3'-dimethoxy-6,6'-bis(diphenylphosphino)-1,1'-biphenyl, 2,2'-dimethyl-6,6'-bis(di-p-tolylphosphino)-1,1'-biphenyl, 2,2'-dimethyl-6,6'-bis(di-p-tert-butylphenylphosphino)-1,1'-biphenyl, 2,2',4,4'-tetramethyl-3,3'-dimethoxy-6,6'-bis(di-p-methoxyphenylphosphino)-1,1'-biphenyl, and the like.

The ligand used in the production method of the present invention may be used as a salt. Such a salt includes, for example, a hydrochloride, a hydrobromide, a tetraphenylborate, a tetrafluoroborate, and the like.

As the ligand used in the production method of the present invention, above all, the phosphine-type ligand is preferable, moreover, the phosphine-type ligand represented by $R^5P(R^6)R^7$ and the phosphine-type ligand represented by $R^8(R^9)PR^{10}P(R^{11})R^{12}$, and the amine-phosphine-type ligand represented by $R^8(R^9)PR^{10}N(R^{11})R^{12}$ are preferable.

As for the phosphine-type ligand represented by $R^5P(R^6)R^7$, $R^5$ and $R^6$ each are independently preferably a $C_3$ to $C_8$ alkyl group or an alicyclic hydrocarbon group, and, in addition, more preferably $R^7$ is a $C_1$ to $C_8$ alkyl group, an alicyclic hydrocarbon group, a $C_6$ to $C_{12}$ aryl group, or a heteroaryl group. Specific examples include tri(tert-butyl)phosphine, tri(cyclohexyl)phosphine, tert-butyldicyclohexylphosphine, di(tert-butyl)cyclohexylphosphine, di(tert-butyl)methylphosphine, 2-(2'-dicyclohexylphosphinophenyl)-1,3-dioxo lane, XPhos, SPhos, RuPhos, cataCXium A, cataCXium ABn, cataCXium PtB, cataCXium PCy, cataCXium POMetB, cataCXium POMeCy, cataCXium PIntB, cataCXium PInCy, cataCXium PICy, Q-Phos, JOSIPHOS tri(n-butyl)phosphine, tri(n-octyl)phosphine, salts thereof, and the like. Above all, phosphine having 0 or 1 hydrogen atoms bonded to each carbon atom of $R^5$ and $R^6$ is preferable, wherein $R^5$ and $R^6$ are bonded to a phosphorus atom. Specific examples include tri(tert-butyl)phosphine, tri(cyclohexyl)phosphine, tort-butyldicyclohexylphosphine, di(tert-butyl)cyclohexylphosphine, di(tert-butyl)methylphosphine, 2-(2'-dicyclohexylphosphinophenyl)-1,3-dioxo lane, XPhos, SPhos, RuPhos, cataCXium A, cataCXium ABn, cataCXium PtB, cataCXium PCy, cataCXium POMetB, cataCXium POMeCy, cataCXium PIntB, cataCXium PInCy, cataCXium PICy, Q-Phos, JOSIPHOS, salts thereof, and the like. Furthermore, $R^7$ is preferably a $C^3$ to $C^8$ alkyl group or an alicyclic hydrocarbon group. For example, tri(tert-butyl)phosphine, di(tert-butyl)methylphosphine, di(tert-butyl)cyclohexylphosphine, tert-butyldicyclohexylphosphine, tricyclohexylphosphine, or salts thereof is preferable, in particular, di(tert-butyl)cyclohexylphosphine or a salt thereof is preferable.

As for the phosphine-type ligand represented by $R^8(R^9)PR^{10}P(R^{11})R^{12}$ and the amine-phosphine-type ligand represented by $R^8(R^9)PR^{10}N(R^{11})R^{12}$, $R^8$ and $R^9$ each independently are preferably a $C_3$ to $C_8$ alkyl group or an alicyclic hydrocarbon group. Moreover, the ligand having 0 or 1 hydrogen atoms bonded to each carbon atom of $R^8$ and $R^9$ is preferable, wherein $R^8$ and $R^9$ are bonded to a phosphorus atom or a nitrogen atom. Examples include 1,1'-bis(tert-butyl)ferrocene, 1,2-bis(dicyclohexylphosphino)ethane, 1,3-(dicyclohexylphosphino)propane, 1,4-bis(dicyclohexylphosphino)butane, 1,2-bis(di-tert-butylphosphino)ethane, 1,3-bis(di-tert-butylphosphino)propane, 1,4-bis(di-tert-butylphosphino)butane, DavePhos, t-Bu-DavePhos, TrippyPhos, BippyPhos, salts thereof, and the like.

Furthermore, the ligand can be used by coordinating to the palladium compound in advance. In such a case, it is preferable to use by coordination of a preferable ligand.

These ligands or salts may be used in mixed combination.

[A Base]

In the course of the reaction, the yield of the compound represented by formula (3) can be increased by concomitant usage of bases. Such bases used in the production method of the present invention are, although not limited thereto, among all, lithium hydride, sodium hydride, potassium hydride, a hydroxide of an alkali metal (lithium hydroxide, sodium hydroxide, potassium hydroxide, and cesium hydroxide), a hydroxide of a Group 2 element (magnesium hydroxide, calcium hydroxide, and barium hydroxide), a fluoride of an alkali metal (lithium fluoride, sodium fluoride, potassium fluoride, and cesium fluoride), a phosphate of an alkali metal (trilithium phosphate, trisodium phosphate, trisodium phosphate, and tricesium phosphate), lithium acetate, sodium acetate, potassium acetate, a carbonate of an alkali metal or a Group 2 element (lithium carbonate, sodium carbonate, potassium carbonate, cesium carbonate, magnesium carbonate, calcium carbonate, and barium carbonate), a hydrogen carbonate of an alkali metal or a Group 2 element (lithium hydrogen carbonate, sodium hydrogen carbonate, potassium hydrogen carbonate, cesium hydrogen carbonate, magnesium hydrogen carbonate, calcium hydrogen carbonate, and barium hydrogen carbonate), a metallic salt of $C_1$ to $C_6$ alkoxide (a lithium salt, a sodium salt, a potassium salt, and a magnesium salt), a metallic salt of $C_1$ to $C_6$ alkyl anion (a lithium salt, a sodium salt, a potassium salt, and a magnesium salt), a halide of tetra($C_1$ to $C_4$ alkyl)ammonium (fluoride, chloride, and bromide), diisopropylethylamine, tributylamine, N-methylmorpholine, diazabicycloundecene, diazabicyclooctane, imidazole, and the like.

The "$C_1$ to $C_6$ alkoxide" in the "metallic salt of the $C_1$ to $C_6$ alkoxide (a lithium salt, a sodium salt, a potassium salt, and a magnesium salt)" used as the base in the production method of the present invention includes methoxide, ethoxide, n-propyloxide, isopropyloxide, n-butyloxide, isobutyloxide, tert-butyloxide, n-pentyloxide, isopentyloxide, neopentyloxide, 1-methylpropyloxide, n-hexyloxide, isohexyloxide, 1,1-dimethylbutyloxide, 2,2-dimethylbutyloxide, 3,3-dimethylbutyloxide, and the like.

The "$C_1$ to $C_6$ alkyl anion" in the "metallic salt of $C_1$ to $C_6$ alkyl anion (a lithium salt, a sodium salt, a potassium salt, and a magnesium salt)" used as the base in the production method of the present invention includes, methyl anion, ethyl anion, n-propyl anion, isopropyl anion, n-butyl anion, isobutyl anion, tert-butyl anion, n-pentyl anion, isopentyl anion, neopentyl anion, 1-methylpropyl anion, n-hexyl anion, isohexyl anion, 1,1-dimethylbutyl anion, 2,2-dimethylbutyl anion, 3,3-dimethylbutyl anion, and the like.

As the base in the production method of the present invention, the hydroxide of the alkali metal or the Group 2 element, the fluoride of the alkali metal, the phosphate of the alkali metal, the carbonate of the alkali metal or the Group 2 element, the hydrogen carbonate of the alkali metal or the Group 2 element, are preferable, above all, the carbonate of the alkali metal or the hydrogen carbonate of the alkali metal are preferable. Moreover, potassium carbonate, potassium hydrogen carbonate, sodium carbonate, sodium hydrogen carbonate, or cesium carbonate is preferable, in particular, potassium carbonate, potassium hydrogen carbonate, sodium carbonate, or sodium hydrogen carbonate is preferable, in addition, potassium carbonate or potassium hydrogen carbonate is particularly preferable.

These bases may be used in mixed combination.

[$C_1$ to $C_{40}$ Carboxylic Acid or a Salt Thereof]

In the course of the reaction, by adding $C_1$ to $C_{40}$ carboxylic acid, the yield of the compound presented by formula (3) and/or the reaction rate can be further increased. The $C_1$ to $C_{40}$ carboxylic acid may be used as a salt. Such a salt includes, for example, alkali metal salts such as a sodium salt, a potassium salt, a lithium salt and the like; salts of Group 2 element, such as a calcium salt, a magnesium salt, and the like; metallic salts such as an aluminum salt, an iron salt, a copper salt, a silver salt, and the like, inorganic salts such as ammonium salt and the like; organic salts like amine salts such as a tert-octylamine salt, a dibenzylamine salt, a morpholine salt, a glucosamine salt, a phenylglycylalkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzylphenylamine salt, a piperazine salt, a tetramethylammonium salt, a tris(hydroxymethyl)aminomethane salt, and the like.

The $C_1$ to $C_{40}$ carboxylic acid has 1 to 40 carbon atoms including the carbon of the carboxyl group, and may contain a halogen atom, an oxo group, and an ether linkage. The examples include formic acid, acetic acid, propionic acid, butanoic acid, 2-methylpropanoic acid, pentanoic acid, 3-methylbutanoic acid, 2-methylbutanoic acid, pivalic acid, 3,3-dimethylbutanoic acid, 2-methylpentanoic acid, 2-methylhexanoic acid, 2-methylheptanoic acid, pentanecarboxylic acid, hexanoic acid, 4-methylpentanoic acid, 3,3-dimethylbutanoic acid, 2-ethylbutanoic acid, 3-methylpentanoic acid, 2,2-dimethylbutanoic acid, 2,3-dimethylbutanoic acid, heptanoic acid, 3-methylhexanoic acid, 4-methylhexanoic acid, 5-methylhexanoic acid, 2,2-dimethylpentanoic acid, 2,3,3-trimethylbutanoic acid, octanoic acid, 2-propylpentanoic acid, 2-ethylhexanoic acid, 3-methylheptanoic acid, 4-methylheptanoic acid, 6-methylheptanoic acid, 2,2-dimethylheptanoic acid, 3-methylheptanoic acid, 2,2-diethylbutanoic acid, 2,2,4-trimethylpentanoic acid, 2-methyloctanoic acid, 2-methylundecanoic acid, 2-methylnonanoic acid, 2-methyldecanoic acid, 2-ethyldecanoic acid, 2,2-dimethylundecanoic acid, 2-ethylundecanoic acid, 2-propyldecanoic acid, 2-hexyldecanoic acid, 2-methylpentadecanoic acid, 2-methylhexadecanoic acid, 2-heptylundecanoic acid, 2-methyloctadecanoic acid, pristanic acid, 2-decyldodecanoic acid, 2-dodecyltetradecanoic acid, 2-tetradecylhexadecanoic acid, 2-hexadecyl-octadecanoic acid, 2-octadecyleicosanoic acid, α-methylcinnamic acid, cyclopropylacetic acid, 3-cyclopropylpropionic acid, cyclobutylacetic acid, cyclopentylacetic acid, cyclohexylacetic acid, cyclopentylpropionic acid, (2-methylcyclopentyl)acetic acid, cyclopentanecarboxylic acid, 3-oxocyclopentanecarboxylic acid, cyclopropanecarboxylic acid, cyclobutanecarboxylic acid, cyclohexanecarboxylic acid, cycloheptanecarboxylic acid, 1-methylcyclopropanecarboxylic acid, 2-methylcyclopropanecarboxylic acid, 2,2-dimethylcyclopropanecarboxylic acid, 2,2,3,3-tetramethylcyclopropanecarboxylic acid, 2-octylcyclopropanecarboxylic acid, 1-(4-methylphenyl)-1-cyclopropanecarboxylic acid, 2-p-toluyl-cyclopropanecarboxylic acid, 1-(2-fluorophenyl)cyclopropanecarboxylic acid, 1-(3-fluorophenyl)cyclopropanecarboxylic acid, 1-(4-fluorophenyl)cyclopropanecarboxylic acid, 1-(4-chlorophenyl)cyclopropanecarboxylic acid, 1-(3-chlorophenyl)cyclopropanecarboxylic acid, 2-(4-chlorophenyl)cyclopropanecarboxylic acid, 1-(2,4-dichlorophenyl)cyclopropanecarboxylic acid, 1-(3,4-dichlorophenyl)cyclopropanecarboxylic acid, 2-fluoro-2-phenylcyclopropanecarboxylic acid, 1-(4-methoxyphenyl)cyclopropanecarboxylic acid, 2-(4-(tert-butyl)phenyl)cyclopropanecarboxylic acid, 2,2-difluorocyclopropanecarboxylic acid, 2,2-dichlorocyclopropanecarboxylic acid, 2-chloro-2-fluorocyclopropanecarboxylic acid, 1-trifluoromethylcyclopropanecarboxylic acid, 2,2-dichloro-1-methylcyclopropanecarboxylic acid, cyclopropane-1,1-dicarboxylic acid, 2,2'-oxydiacetic acid, 2,3-dimethylcyclopropanedicarboxylic acid, 2,2-dimethylmalonic acid, 2,3-dimethylsuccinic acid, 2,2,3-trimethylsuccinic acid, 2,2,3,3-tetramethylsuccinic acid, 2,4-dimethylglutaric acid, 2,2,4-trimethylglutaric acid, 2,2,4,4-tetramethylglutaric acid, 2,5-dimethyladipic acid, 2,2,5-trimethyladipic acid, 2,2,5,5-tetramethyladipic acid, 2,6-dimethylpimelic acid, 2,2,6-trimethylpimelic acid, 2,2,6,6-tetramethylpimelic acid, 4-methylcyclobutanecarboxylic acid, 4-ethylcyclopropanecarboxylic acid, 3-methoxycyclobutanecarboxylic acid, 3-chlorocyclobutanecarboxylic acid, 4-chlorobutanecarboxylic acid, 3-oxo-cyclobutanecarboxylic acid, 3,3-dimethylcyclobutanecarboxylic acid, 1-methylcyclopentanecarboxylic acid, 3-cyclopentenecarboxylic acid, 1-methylcyclopentanecarboxylic acid, 1-methylcyclohexanecarboxylic acid, 4-methylcyclohexanecarboxylic acid, 2-methylcyclohexanecarboxylic acid, 3-methylcyclohexanecarboxylic acid, cyclooctanecarboxylic acid, spiro[2.2]pentane-1-carboxylic acid, spiro[2.3]hexane-1-carboxylic acid, bicyclo[4.1.0]heptane-7-carboxylic acid, tricyclo[3.2.1.0$^{2,4}$] octane-3-carboxylic acid, bicyclo[6.1.0]nonane-9-carboxylic acid, bicyclo[2.2.1]heptane-1-carboxylic acid, bicyclo [2.2.1]heptane-2-carboxylic acid, 7,7-dimethyltricyclo [2.2.1.0$^{2,6}$]heptane-1-carboxylic acid, 5-norbornene-2-carboxylic acid, norbornane-2-carboxylic acid, 1-adamantanecarboxylic acid, 3-methyl-adamantane-1-carboxylic acid, 3-fluoroadamantane-1-carboxylic acid, 3,5-dimethyladamantane-1-carboxylic acid, 3-ethyladamantane-1-carboxylic acid, 3-chloroadamantane-1-carboxylic acid, 3,5,7-trimethyladamantane-1-carboxylic acid, 3-bromoadamantane-1-carboxylic acid, 5-bromo-3-methyladamantane- 1-carboxylic acid, 5-bromo-3-ethyladamantane-1-carboxylic acid, tetrahydrofuran-2-carboxylic acid, tetrahydrofuran-3-carboxylic acid, tetrahydropyran-4-carboxylic acid, tetrahydropyran-3-carboxylic acid, methoxyacetic acid, trichloroacetic acid, dichloroacetic acid, chloroacetic acid, fluoroacetic acid, 2-fluoro-2-methylpropanoic acid, difluoroacetic acid, 2-chloropropanoic acid, 3-fluoropropionic acid, 2-fluoropropionic acid, 2-chloropropionic acid, 3-chloropropionic acid, 2-chlorobutanoic acid, 3-chlorobutanoic acid, 4-chlorobutanoic acid, 2-chloro-2-methylpropanoic acid, 3-chloro-2,2-dimethylpropanoic acid, 5-chloropentanoic acid, 2-chloro-3-methylbutanoic acid, dichloroacetic acid, 1-fluoro-1-chloroacetic acid, 2,2-difluoropropionic acid, 2,2-difluorobutanoic acid, 2,2-dichloropropionic acid, 2,3-dichloropropionic acid, chlorodifluoroacetic acid, trifluoroacetic acid, 3,3,3-trifluoropropionic acid, 2-methyl-4,4,4-trifluorobutanoic acid, 4,4,4-trifluorobutanoic acid, 2,2,3,3-tetrafluoropropionic acid, 2,3,3,3,-tetrafluoropropionic acid, and the like. However, the present invention is not limited thereto.

As the $C_1$ to $C_{40}$ carboxylic acid in the production method of the present invention, the carboxylic acid is preferred wherein the carbon atom of the carboxylic group at the α-position is not the carbon atom on the aromatic ring. Examples include acetic acid, propionic acid, 2-methylpropanoic acid, 2-ethylbutanoic acid, pivalic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, 2-methyldecanoic acid, 2-ethyldecanoic acid, 2,2-dimethylundecanoic acid, 2-ethylundecanoic acid, 2-propyldecanoic acid, 2-hexyldecanoic acid, 2-methylpentadecanoic acid, 2-methylhexadecanoic acid, 2-heptylundecanoic acid, 2-methyloctadecanoic acid, pristanic acid, 2-decyldodecanoic acid, 2-dodecyltetradecanoic acid, 2-tetradecylhexadecanoic acid, 2-hexadecyloctadecanoic acid, 2-octadecyleicosanoic acid, 3,5-dimethyladamantane-1-carboxylic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, 2,2'-oxydiacetic acid, 2,3-dimethylcyclopropanedicarboxylic acid, 2,3-dimethylcyclopropanedicarboxylic acid, 2,2-dimethylmalonic acid, 2,3-dimethylsuccinic acid, 2,2,3-trimethylsuccinic acid, 2,2,3,3-tetramethylsuccinic acid, 2,4-dimethylglutaric acid, 2,2,4-trimethylglutaric acid, 2,2,4,4-tetramethylglutaric acid, 2,5-dimethyladipic acid, 2,2,5-trimethyladipic acid, 2,2,5,5-tetramethyladipic acid, 2,6-dimethylpimelic acid, 2,2,6-trimethylpimelic acid, 2,2,6,6-tetramethylpimelic acid, cyclopropane-1,1-dicarboxylic acid, and the like.

Above all, the $C_1$ to $C_{40}$ carboxylic acid having 0 or 1 hydrogen atoms bonded to the carboxyl group at the α-position is more preferable. Examples include 2-methylpropanoic acid, 2-ethylbutanoic acid, pivalic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, 2-methyldecanoic acid, 2-ethyldecanoic acid, 2,2-dimethylundecanoic acid, 2-ethylundecanoic acid, 2-propyldecanoic acid, 2-hexyldecanoic acid, 2-methylpentadecanoic acid, 2-methylhexadecanoic acid, 2-heptylundecanoic acid, 2-methyloctadecanoic acid, pristanic acid, 2-decyldodecanoic acid, 2-dodecyltetradecanoic acid, 2-tetradecylhexadecanoic acid, 2-hexadecyloctadecanoic acid, 2-octadecyleicosanoic acid, 3,5-dimethyladamantane-1-carboxylic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, 2,3-dimethyl-cyclopropanedicarboxylic acid, 2,2-dimethylmalonic acid, 2,3-dimethylsuccinic acid, 2,2,3-trimethylsuccinic acid, 2,2,3,3,-tetramethylsuccinic acid, 2,4-dimethylglutaric acid, 2,2,4-trimethylglutaric acid, 2,2,4,4-tetramethylglutaric acid, 2,5-dimethyladipic acid, 2,2,5-trimethyladipic acid, 2,2,5,5-tetramethyladipic acid, 2,6-dimethylpimelic acid, 2,2,6-trimethylpimelic acid, 2,2,6,6-tetramethylpimelic acid, cyclopropane-1,1-dicarboxylic acid, and the like.

Furthermore, the $C_1$ to $C_{40}$ carboxylic acid having one carboxyl group is preferable. Examples include 2-methylpropanoic acid, 2-ethylbutanoic acid, pivalic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, 2-methyldecanoic acid, 2-ethyldecanoic acid, 2,2-dimethylundecanoic acid, 2-ethylundecanoic acid, 2-propyldecanoic acid, 2-hexyldecanoic acid, 2-methylpentadecanoic acid, 2-methylhexadecanoic acid, 2-heptylundecanoic acid, 2-methyloctadecanoic acid, pristanic acid, 2-decyldodecanoic acid, 2-dodecyltetradecanoic acid, 2-tetradecylhexadecanoic acid, 2-hexadecyloctadecanoic acid, 2-octadecyleicosanoic acid, 3,5-dimethyladamantane-1-carboxylic acid, cyclopropanoic acid, 2,2,3,3-tetramethylcyclopropanoic acid, cyclopentanoic acid, 1-adamantanecarboxylic acid, 2-chloro-2-methylpropanoic acid, tetrahydrofuran-2-carboxylic acid, and the like.

Particularly, the $C_1$ to $C_{40}$ carboxylic acid consisting of only carbon atoms and hydrogen atoms except the carboxyl group is more preferable. Examples include 2-methylpropanoic acid, 2-ethylbutanoic acid, pivalic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, 2-methyldecanoic acid, 2-ethyldecanoic acid, 2,2-dimethylundecanoic acid, 2-ethylundecanoic acid, 2-propyldecanoic acid, 2-hexyldecanoic acid, 2-methylpentadecanoic acid, 2-methylhexadecanoic acid, 2-heptylundecanoic acid, 2-methyloctadecanoic acid, pristanic acid, 2-decyldodecanoic acid, 2-dodecyltetradecanoic acid, 2-tetradecylhexadecanoic acid, 2-hexadecyloctadecanoic acid, 2-octadecyleicosanoic acid, 3,5-dimethyladamantane-1-carboxylic acid, cyclopropanoic acid, 2,2,3,3-tetramethylcyclopropanoic acid, cyclopentanoic acid, 1-adamantanecarboxylic acid, and the like.

Above all, the $C_1$ to $C_{34}$ carboxylic acid is more preferable; in particular, $C_1$ to $C_{12}$ carboxylic acid is more preferable. Examples include 2-methylpropanoic acid, 2-ethylbutanoic acid, pivalic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, cyclopropanoic acid, 2,2,3,3-tetramethylcyclopropanoic acid, cyclopentanoic acid, 1-adamantanecarboxylic acid, and the like. Above all, 2-methylpropanoic acid or pivalic acid is preferable.

As a $C_1$ to $C_{40}$ carboxylic acid or a salt thereof, these $C_1$ to $C_{40}$ carboxylic acids or salts thereof may be used in combination.

[An Additive]

In the course of the reaction, by adding at least one additive selected from the group consisting of copper, silver, and salt thereof, the improvement of the yield of the compound represented by formula (3), the improvement of the reaction rate, the reduction in the amount of the palladium compound, and/or the suppression of side reactions, and the like can be achieved.

Copper and salts thereof include zerovalent copper, a monovalent copper salt, and a divalent copper salt. In particular, zerovalent copper or a monovalent copper salt is preferred. The monovalent copper salts include, for example, copper(I) halides (copper(I) fluoride, copper(I) chloride, copper(I) bromide, and copper(I) iodide), copper(I) carboxylates (copper(I) formate, copper(I) acetate, copper(I) propionate, copper(I) 2-methylpropanoate, copper(I) 2-ethylbutanoate, copper(I) 2-methylbutanoate, copper(I) 2-methylpentanoate, copper(I) 2-methylhexanoate, copper(I) 2-methylheptanoate, copper(I) 2,2-dimethylbutanoate, copper(I) 2,3-dimethylbutanoate, copper(I) 2,2-dimethylpentanoate, copper(I) 2,3,3-trimethylbutanoate, copper(I) 2-ethylhexanoate, copper(I) 2,2-diethylbutanoate, copper(I) 2,2,4-trimethylpentanoate, copper(I) 2-methyloctanoate, copper(I) 2-methylundecanoate, copper(I) 2-methylnonanoate, copper(I) pivalate, copper(I) cyclopropanoate, copper(I) 2,2,3,3-tetramethylcyclopropanoate, copper(I) cyclopentanoate, copper(I) 1-adamantanecarboxylate, and the like, although not limited thereto), copper(I) tetrafluoroborate, copper(I) sulfate, copper(I) nitrate, copper(I) cyanide, copper(I) thiocyanide, copper(I) phosphate, copper(I) oxide, copper(I) sulfide, hydrates thereof, and the like.

Above all, copper(I) oxide, copper (I) halides, or copper(I) carboxylates is preferable. In particular, copper(I) chloride, copper(I) bromide, copper(I) 2-methylpropanoate or copper (I) pivalate are preferable.

Silver and salts thereof include zerovalent silver, a monovalent silver salt, and a divalent silver salt, and above all, zerovalent silver or a monovalent silver salt is preferred. The monovalent silver salts include, for example, silver(I) halides (silver(I) fluoride, silver(I) chloride, silver(I) bromide, silver (I) iodide), silver(I) carboxylates (silver(I) formate, silver(I) acetate, silver(I) propionate, silver(I) 2-methylpropanoate, silver(I) 2-ethylbutanoate, silver(I) 2-methylbutanoate, silver (I) 2-methylpentanoate, silver(I) 2-methylhexanoate, silver (I) 2-methylheptanoate, silver(I) 2,2-dimethylbutanoate, silver(I) 2,3-dimethylbutanoate, silver(I) 2,2-dimethylpentanoate, silver(I) 2,3,3-trimethylbutanoate, silver(I) 2-ethylhexanoate, silver(I) 2,2-diethylbutanoate, silver(I) 2,2,4-trimethylpentanoate, silver(I) 2-methyloctanoate, silver(I) 2-methylundecanoate, silver(I) 2-methylnonanoate, silver(I) pivalate, silver(I) cyclopropanoate, silver (I) 2,2,3,3-tetramethylcyclopropanoate, silver(I) cyclopentanoate, silver(I) 1-adamantanecarboxylate, and the like, although not limited thereto), silver(I) tetrafluoroborate, silver(I) sulfate, silver(I) nitrate, silver(I) cyanide, silver(I) thiocyanide, silver(I) carbonate, silver(I) phosphate, silver(I) oxide, silver(I) sulfide, silver(I) $C_1$ to $C_6$ alkoxylate, hydrates thereof, and the like.

Above all, silver(I) oxide, silver(I) halide, or silver(I) carboxylate is preferable. In particular, silver(I) chloride, silver (I) bromide, silver(I) 2-methylpropanoate, or silver(I) pivalate is preferable.

Copper, silver, and salts thereof used in the production method of the present invention as the additive may be used by forming complexes. Such examples include a dimethylsulfide complex, a triphenylphosphine complex, a trimethylphosphine complex, a tetrahydrofuran complex, and the like.

These additives may be used in combination.

Instead of using the "palladium compound" and the "$C_1$ to $C_{40}$ carboxylic acid or salts thereof" independently, carboxylic acid salts of the palladium compound (for example, palladium(II) propionate) or complexes thereof may be used when they are commercially available or easy to prepare. Similarly, the carboxylic acid salt of copper or silver, or complexes thereof may be used instead of using the "$C_1$ to $C_{40}$ carboxylic acid or salts thereof" and the "additive" independently. Such $C_1$ to $C_{40}$ carboxylic acid salts include salts of divalent palladium, monovalent copper, or monovalent silver.

When a palladium compound salt, a copper salt, a silver salt of the $C_1$ to $C_{40}$ carboxylic acid, or a complex thereof is used, the "$C_1$ to $C_{40}$ carboxylic acid or a salt thereof" may be additionally used.

In the divalent palladium salt, a monovalent copper salt, or a monovalent silver salt of the $C_1$ to $C_{40}$ carboxylic acid, which is commercially available or easy to prepare, examples of the $C_1$ to $C_{40}$ carboxylic acid include formic acid, acetic acid, propionic acid, 2-methylpropanoic acid, 2-ethylbutanoic acid, 2-methylbutanoic acid, 2-methylpentanoic acid, 2-methylhexanoic acid, 2-methylheptanoic acid, 2,2-dimethylbutanoic acid, 2,3-dimethylbutanoic acid, 2,2-dimethylpentanoic acid, 2,3,3-trimethylbutanoic acid, 2-ethylhexanoic acid, 2,2-diethylbutanoic acid, 2,2,4-trimethylpentanoic acid, 2-methyloctanoic acid, 2-methylundecanoic acid, 2-methylnonanoic acid, pivalic acid, cyclopropanoic acid, 2,2,3,3-tetramethylcyclopropanoic acid, cyclopentanoic acid, 1-adamantanecarboxylic acid, and the like.

In the production method of the present invention, a reducing agent for reducing palladium compounds may be used in conjunction with the palladium compound. Examples include zinc, magnesium, triethylsilane, and silane supported by a resin or silica gel, and the like.

In the production method of the present invention, an antioxidant that prevents the oxidation of palladium compounds may be used in conjunction with the palladium compound. Examples include ascorbic acid and the like.

The production method of the present invention can be carried out in a broad range of temperature. Generally, the production method is performed at 0° C. to 200° C. preferably at 0° C. to 150° C. Furthermore, the reaction under ordinary pressure is desirable, however, the process can be carried out under increased or reduced pressure. The reaction time is 0.1 to 144 hours, preferably 0.1 to 48 hours. The reaction can be performed in air, however, the reaction under a gas that does not have adverse effects on the reaction such as argon gas, nitrogen gas, and the like is desirable. Moreover, microwave irradiation may be applied in the reaction of the present invention.

Solvents used in the present invention include, although it is not particularly limited thereto, aliphatic hydrocarbons (pentane, hexane, cyclohexane, heptane, octane, nonane, decane, undecane, dodecane, cycloheptane, cyclooctane, and the like), aliphatic halogenated hydrocarbons (dichloromethane, chloroform, carbon tetrachloride, dichloroethane, and the like), aromatic hydrocarbons (benzene, toluene, xylene, mesitylene, chlorobenzene, and the like), ethers (diethyl ether, dibutyl ether, dimethoxyethane (DME), cyclopentyl methyl ether (CPME), tert-butyl methyl ether, tetrahydrofuran, dioxane, diethylene glycol dimethyl ether, and the like), ketones (acetone, methyl isobutyl ketone, and the like), esters (ethyl acetate, ethyl propionate, and the like), acid amides (dimethylformamide (DMF), dimethylacetamide (DMA), N-methylpyrrolidone (NMP), and the like), nitriles (acetonitrile, propionitrile, and the like), dimethyl sulfoxide (DMSO), water, mixed solvents thereof, and the like.

Above all, aliphatic hydrocarbons, aromatic hydrocarbons, ethers, ketones, esters, mixed solvents thereof, or the like is preferable.

The amount of the compound of formula (2) relative to the compound of formula (1) used in the production method of the present invention may be in a range from 1 mole % to 1000 mole %. The range is preferably 50 mole % to 200 mole %, more particularly, the range from 75 mole % to 125 mole % is preferable.

The amount of the palladium compound, the ligand or salts thereof, or the $C_1$ to $C_{40}$ carboxylic acid or salts thereof used in the production method of the present invention may be in a range of 100 mole % or less relative to the compound of formula (1) or the compound of formula (2). Preferably the range is 0.001 mole % to 20 mole %, more preferably, 0.01 mole % to 5 mole %.

The amount of the additive used in the production method of the present invention may be in a range of 1000 mole % or less relative to the compound of formula (1) or the compound of formula (2). Preferably, it is 0.001 mole % to 100 mole %, more preferably, 0.01 mole % to 20 mole %.

The amount of the base used in the production method of the present invention may be in a range of 1000 mole % or less relative to the compound of formula (1) or the compound of formula (2). Preferably, it is in a range of 25 mole % to 500 mole %.

The amount of the solvent used in the production method of the present invention may be 1000 times or less in weight relative to the compound of formula (1) or the compound of formula (2). Preferably, it is 0.1 times to 100 times. More preferably, it is 0.1 times to 20 times. Furthermore, 0.5 times to 20 times is more preferable.

The order of addition of the compound of formula (1), the compound of formula (2), the palladium compound, the ligand or a salt thereof, the base, the $C_1$ to $C_{40}$ carboxylic acid or a salt thereof, the additive, and the solvent used in the production process of the present invention is arbitrary and the most appropriate order may be selected depending on the combination of the reagents used.

The "mole %" represents a concentration of a certain material, which is calculated by dividing the number of moles of the material by 100 mole of the relevant material.

The compound represented by formula (1) used in the production method of the present invention can be prepared by the following methods.

Synthesis Method (1)

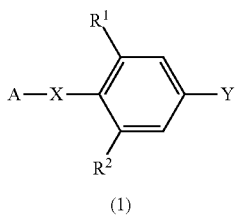

(1)

In the reaction formula, X represents an oxygen atom, and the definition of $R^1$, $R^2$, A, and Y is the same as defined in formula (1). $L^1$ represents a leaving group and includes a halogen atom, a methanesulfonyloxy group, a trifluoromethanesulfonyloxy group, a p-toluenesulfonyloxy group, and the like.

Specifically, the compound represented by formula (1) can be produced by reacting the compound (a) with the compound (b) in the presence of a suitable base in a suitable solvent under a suitable temperature condition.

The solvents used are not particularly limited and include, for example, aliphatic hydrocarbons (hexane, cyclohexane, heptane, and the like), aliphatic halogenated hydrocarbons (dichloromethane, chloroform, carbon tetrachloride, dichloroethane, and the like), aromatic hydrocarbons (benzene, toluene, xylene, chlorobenzene, mesitylene, and the like), ethers (diethyl ether, dibutyl ether, dimethoxyethane (DME), cyclopentyl methyl ether (CPME), tetrahydrofuran, dioxane, and the like), esters (ethyl acetate, ethyl propionate, and the like), acid amides (dimethylformamide (DMF), dimethylacetamide (DMA), N-methylpyrrolidone (NMP), and the like), nitriles (acetonitrile, propionitrile, and the like), dimethyl sulfoxide (DMSO), water, mixed solvent thereof, and the like.

The bases used include, for example, lithium hydride, sodium hydride, potassium hydride, sodium hydroxide, potassium hydroxide, sodium carbonate, potassium carbonate, cesium carbonate, potassium fluoride, cesium fluoride, tripotassium phosphate, sodium acetate, potassium acetate, and the like, metallic salts of a $C_1$ to $C_6$ alkoxides (lithium salt, sodium salt, and potassium salt), metallic salts of a $C_1$ to $C_6$ alkyl anion (lithium salt, sodium salt, and potassium salt), diisopropylethylamine, tributylamine, N-methylmorpholine, diazabicycloundecene, diazabicyclooctane, imidazole, and the like.

For example, the synthesis can be carried out by referring to Reference Examples of the present invention or the methods described in "Bioorg. Med. Chem. Lett. 2004: 14, 2547-2550", and the like.

Synthesis Method (2)

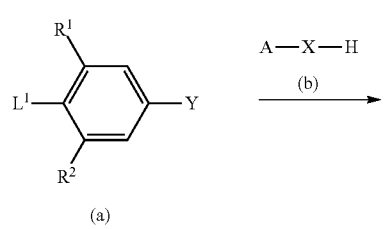

(a)

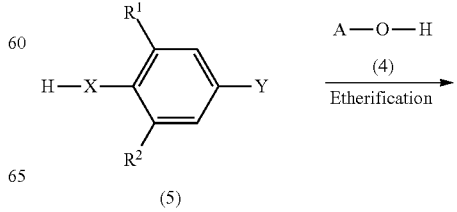

(5)

Compound 14

Compound 15

-continued

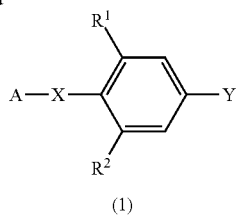

(1)

It the reaction formula, X represents an oxygen atom, and the definition of $R^1$, $R^2$, A, and Y is the same as defined in formula (1). In this reaction, the Mitsunobu reaction can be employed. For example, the reaction can be carried out in the presence of diethyl azodicarboxylate (DEAD), diisopropyl azodicarboxylate (DIAD), 1,1'-(azodicarbonyl)dipiperidine (ADDP), 1,1'-azobis(N,N-dimethylformamide) (TMAD), or the like, and in the presence of triphenylphosphine, tributylphosphine or the like, in a solvent such as tetrahydrofuran, diethyl ether, 1,2-dimethoxyethane, dichloromethane, or toluene and the like at a temperature ranging from 0° C. to 150° C.

The compound represented by formula (1) can be synthesized by reacting using the Mitsunobu reaction and its related reactions described in "Bull. Chem. Soc. Jpn. 1967: 40, 2380", "Synthesis 1981: 1", and "Org. React. 1992: 42, 335"

The compound represented by formula (1) can also be synthesized by using other existing generally known ether synthesis methods. For example, by referring to general textbooks on the organic synthesis such as "Jikken Kagaku Koza 20, 4th Ed., Organic synthesis II, alcohols and amines, pp. 187-205, Ed., The Chemical Society of Japan (Maruzen Co., Ltd.)" and the like.

Among the compounds represented by formula (2), the compound having a thiazole ring as B can be synthesized, for example, by referring to the following schemes, although they are commercially available in some cases.

Compound 16

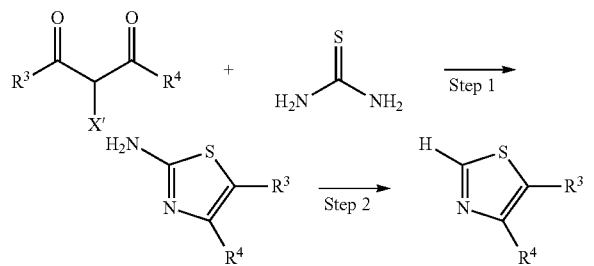

In the above-mentioned reaction scheme, the definition of $R^3$ and $R^4$ is the same as defined in formula (2) of the present invention. X' represents a halogen atom.

2-Aminothiazole derivatives synthesized by the thiazole cyclization reaction of Step 1 in the above-mentioned scheme can be synthesized by referring to the methods described in "Pharmaceutical Chemistry Journal 2007, 41, 105-108", "Pharmaceutical Chemistry Journal 2001: 35, 96-98", "WO 2005/075435", "WO 2005/026137", and the like. The reaction of Step 2 in the above-mentioned scheme can be carried out by referring to "Journal of Heterocyclic Chemistry, 1985: 22, 1621-1630", "Journal of the Chemical Society, Perkin Transactions 1: Organic and Bio-Organic Chemistry, 1982: 1, 159-164", and "Bioorganic & Medicinal Chemistry Letters, 2008: 18, 6231-6235". In addition, for example, the thiazole derivative represented by formula (2) can be synthesized by referring to "WO 2002/051849" and "WO 2001/062250".

Among the compounds represented by formula (2), various compounds having a pyridine ring as B are commercially available, and many synthetic methods of these compounds have been reported as well as available for purchase, therefore, these compounds can be synthesized by using those techniques.

Among the compounds represented by formula (2), the compound wherein B is an isoxazole ring or an isothiazole ring (in formula (2), W represents an oxygen atom or a sulfur atom), although they are commercially available in some cases, can be synthesized by referring, for example, to the methods described in "Tetrahedron Letters 1968: 5209-5213", "Synthesis 1970: 344-350", "Angewandte Chemie 1967: 79, 471-472" and "Chemische Berichte, 1973: 106, 3291-3311".

When the compound represented by formula (3) in the present invention is used as an intermediate, the phenyl-substituted heterocyclic derivative as the final product can be obtained by a hydrolysis reaction and the like.

EXAMPLES

The present invention will be specifically illustrated by the following examples. However, the scope of the present invention is not limited in any sense by these examples.

In the present examples, the following instruments and the like were used for analysis and purification.
TLC: E. Merck silica gel 60 F254 (0.25 mm)
Flash column chromatography: Biotage Flash, Si40
Liquid Chromatography/Mass Spectrometry (LC/MS)
Analytical System: SHIMAZU LCMS-2010A
Software: LCMS Solution
Experimental Condition:
Column: Phenomenex Gemini 3 μm 4.6 mm×30 mm
Flow rate: 1.2 mL/min
Measurement Temperature: 40° C.
A Solvent: 5% MeCN/95% $H_2O$+0.05% TFA
B Solvent: 95% MeCN/5% $H_2O$+0.05% TFA
MS-mode: ESI+
ESI Voltage: 4.5 KV
Source Temp: 130° C.
Desolvation Temp: 320° C.

TABLE 8

| Time [min] | A [%] | B [%] | Flow [ml/min] |
| --- | --- | --- | --- |
| 1 | 0.01 | 95 | 5 | 1.2 |
| 2 | 0.3 | 60 | 40 | 1.2 |
| 3 | 2.3 | 0 | 100 | 1.2 |
| 4 | 3.8 | 0 | 100 | 1.2 |
| 5 | 4.0 | 95 | 5 | 1.2 |
| 6 | 4.5 | 95 | 5 | 0 |

A dual column system was employed.
High Performance Liquid Chromatography (HPLC)
Analytical System: G1315A Hewlett Packard series1100
Software: ChemStation for LC 3D
Experimental Condition:
Column: Phenomenex Luna Phenyl-Hexyl 5 μm 4.6×100 mm
Flow rate: 1.0 mL/min
Wave Length: 240 nm
Measurement Temperature: 40° C.
A Solvent: 5% MeCN/95% $H_2O$+0.05% TFA
B Solvent: 95% MeCN/5% $H_2O$+0.05% TFA
Gradient:
0⇒ 1 min 10% B Solvent
1⇒ 4 min 10⇒ 70% B Solvent 14⇒ 24 min 70⇒ 80% B Solvent
24⇒ 25 min 80⇒ 100% B Solvent
25⇒ 30 min 100% B Solvent
30⇒ 32 min 100⇒ 10% B Solvent
32⇒ 35 min 10% B Solvent Nuclear magnetic resonance (NMR): JEOL JNM-AL400 ($^1$H 400 MHz) $^1$H-NMR shift values are shown in ppm by using tetramethyl silane shift value (δ 0.0 ppm) as a standard value. The data were described as the following abbreviations.

s=singlet, d=doublet, dd=doublet of doublets, t=triplet, q=quartet, br=broad signal).

The proton signal of the carboxylic acid in the $^1$H-NMR spectra in Reference Examples and Examples may not be able to confirmed depending on the measurement condition such as solvent and the like.

Reference Example 1

Synthesis of 5-bromo-2-isobutoxybenzonitrile

Compound 17

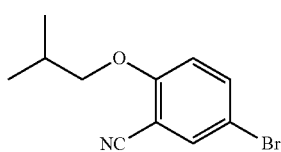

After cooling a suspension of sodium hydride (1.64 g, 60% suspension in mineral oil, 37.5 mmol) in N,N-dimethylformamide (50 mL) to 0° C., 2-methyl-1-propanol (3.47 mL, 37.5 mmol) was added stepwise. And the reaction mixture was stirred at 25° C. for 20 minutes. Again, the reaction mixture was cooled to 0° C., 2-fluoro-5-bromobenzonitrile (5.00 g, 25.0 mmol) was added stepwise to the reaction mixture and the mixture was stirred at 25° C. for 15 hours. After the completion of the reaction, water (100 mL) was added and the mixture was extracted with ethyl acetate (3×100 mL). The combined organic layer was washed with saturated brine (2×50 mL), and dried over sodium sulfate anhydrous. After removing sodium sulfate by filtration, the solvent was evaporated under reduced pressure, and the resulting crude compound was purified on silica-gel chromatography (hexane/ethyl acetate=9/1) to obtain the titled compound (6.04 g). Yield: 95%.

$^1$H-NMR (400 MHz, CDCl$_3$) δ 7.65 (d, J=2.4 Hz, 1H), 7.60 (d, J=9.0 Hz, 2.4 Hz, 1H), 6.84 (d, J=8.8 Hz, 1H), 3.81 (d, J=6.6 Hz, 2H), 2.22-2.12 (m, 1H), 1.06 (d, J=6.6 Hz, 6H).

Example 1

Synthesis of ethyl 2-(3-cyano-4-isobutoxyphenyl)-4-methylthiazole-5-carboxylate

Compound 18

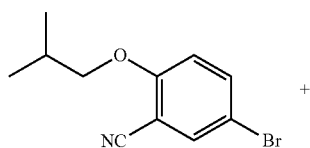

+

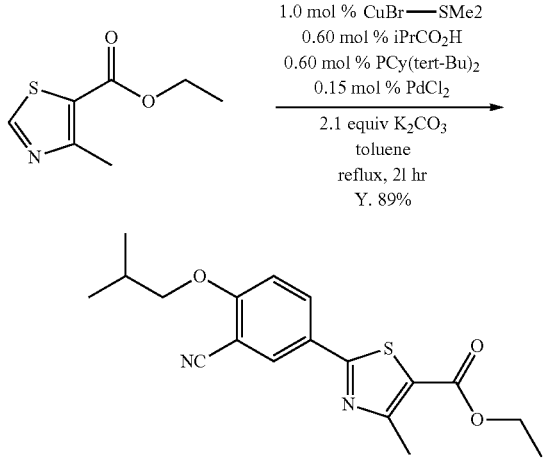

To a reaction vessel were added 5-bromo-2-isobutoxybenzonitrile (5.08 g, 20.0 mmol) obtained in the Reference Example 1, ethyl 4-methylthiazole-5-carboxylate (3.60 g, 21.0 mmol), palladium chloride (5.3 mg, 0.030 mmol), di(tert-butyl)cyclohexylphosphine (27.4 mg, 0.120 mmol), 2-methylpropanoic acid (10.6 mg, 0.120 mmol), copper(I) bromide-dimethylsulfide complex (41.1 mg, 0.20 mmol), potassium carbonate (5.80 g, 42.0 mmol), and toluene (15.2 mL), and the mixture was stirred at 25° C. for 5 minutes under a nitrogen gas atmosphere, further heated to reflux followed by stirring for 21 hours. After the completion of the reaction, hot filtration was carried out to remove insoluble matter. The filtrate was concentrated under reduced pressure, and the resulting crude compound was purified to obtain the titled compound (6.11 g). Yield: 89%.

$^1$H-NMR (400 MHz, CDCl$_3$) δ 8.18 (d, J=2.44 Hz, 1H), 8.09 (dd, J=8.78 Hz, 2.20 Hz, 1H), 7.01 (d, J=8.78 Hz, 1H), 4.36 (q, J=7.07 Hz, 2H), 3.90 (d, J=6.34 Hz, 2H), 2.77 (s, 3H), 2.26-2.16 (m, 1H), 1.39 (t, J=7.19 Hz, 3H), 1.09 (d, J=6.83 Hz, 6H).

Example 2

Synthesis of ethyl 2-(3-cyano-4-isobutoxyphenyl)-4-methylthiazole-5-carboxylate

Compound 19

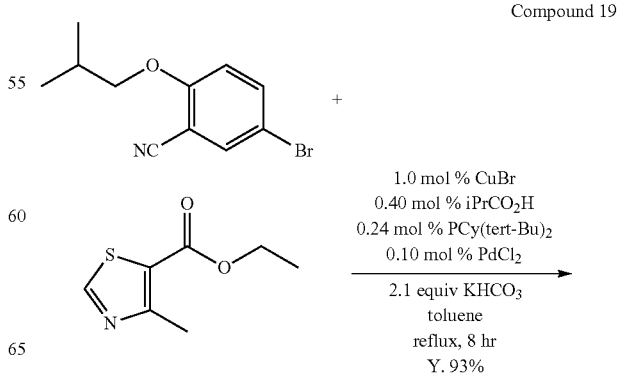

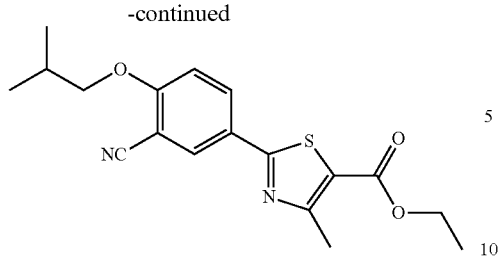

To a reaction vessel were added 5-bromo-2-isobutoxybenzonitrile (5.08 g, 20.0 mmol) obtained in the Reference Example 1, ethyl 4-methylthiazole-5-carboxylate (3.60 g, 21.0 mmol), palladium chloride (3.5 mg, 0.020 mmol), di(tert-butyl)cyclohexylphosphine (11.0 mg, 0.048 mmol), 2-methylpropanoic acid (7.0 mg, 0.080 mmol), copper(I) bromide (28.7 mg, 0.20 mmol), potassium hydrogen carbonate (4.21 g, 42.0 mmol), and toluene (15.2 mL), the mixture was stirred at 25° C. for 5 minutes under a nitrogen gas atmosphere, further heated to reflux, and stirred for 8 hours. After the completion of the reaction, the mixture was hot filtrated to remove insoluble matter. The resulting crude compound was purified to obtain the titled compound (6.38 g). Yield 93%.

Example 3

Synthesis of ethyl 2-(3-cyano-4-isobutoxyphenyl)-4-methylthiazole-5-carboxylate Compound 20

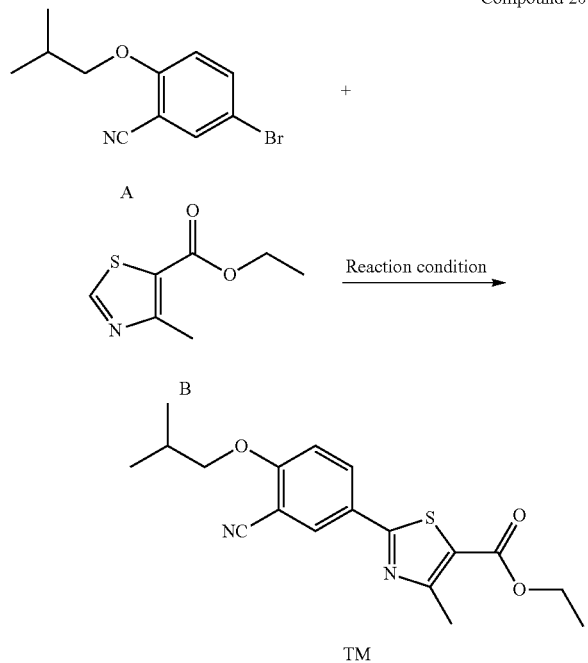

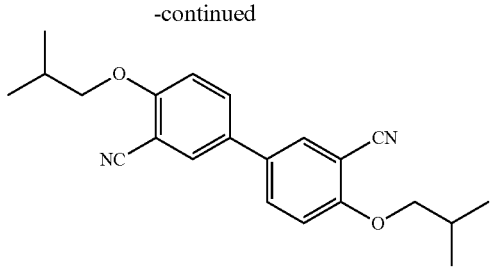

To a test tube-type reaction vessel (60 mL) were added ethyl 4-methylthiazole-5-carboxylate (2.14 g, 12.5 mmol), 5-bromo-2-isobutoxybenzonitrile (2.54 g, 10.0 mmol) obtained in the Reference Example 1 and xylene (7.6 mL). After adding compounds listed in the Table 9 as a palladium compound (0.025 mmol), a ligand (0.10 mmol), a base (21.0 mmol), a carboxylic acid (0.10 mmol), and an additive (1.0 mmol), the reaction vessel was filled with nitrogen gas and sealed air-tight. The reaction mixture was heated to 140° C. and stirred for 24 hours. After the completion of the reaction, a part of the reaction solution was diluted with xylene and DMSO and the resulting solution was analyzed by HPLC measurement. The total HPLC area % of the compound A to D and TM (TM means target compound) was adjusted to 100%, the calculated yield of the subject material was calculated from each HPLC area %. Calculation of the yield from the HPLC area % of the subject material was carried out by applying corresponding numbers in the following calculation formula.

Yield (%) of TM=total amount of TM (mol)/[{total amount of A (mol)+total amount of C (mol)×2+ total amount of TM (mol)}]×100

Total amount of each compound (mol)=HPLC area value (mAU) of each compound/HPLC area value (mAU/mol) per mol of each compound The results are shown in the Table 9.

TABLE 9

| Experimental No. | Reaction condition | | | | | HPLC area % | | | | | Calculated Yield (%) |
|---|---|---|---|---|---|---|---|---|---|---|---|
| | Base | Palladium | Ligand | Carboxylic acid | Additive | TM | A | B | C | D | TM |
| 1 | — | PdCl$_2$ | tBu$_2$PCy | iPrCO$_2$H | CuBr—SMe$_2$ | 0.1 | 56.1 | 43.5 | 0.0 | 0.3 | 0.0 |
| 2 | K$_2$CO$_3$ | — | tBu$_2$PCy | iPrCO$_2$H | CuBr—SMe$_2$ | 0.3 | 55.6 | 44.1 | 0.0 | 0.0 | 0.2 |
| 3 | K$_2$CO$_3$ | PdCl$_2$ | — | iPrCO$_2$H | CuBr—SMe$_2$ | 7.7 | 50.4 | 41.2 | 0.2 | 0.6 | 5.9 |
| 4 | K$_2$CO$_3$ | PdCl$_2$ | tBu$_2$PCy | — | CuBr—SMe$_2$ | 4.2 | 53.4 | 42.1 | 0.0 | 0.3 | 3.2 |

TABLE 9-continued

| Experimental No. | Reaction condition | | | | | HPLC area % | | | | | Calculated Yield (%) |
| --- | --- | --- | --- | --- | --- | --- | --- | --- | --- | --- | --- |
| | Base | Palladium | Ligand | Carboxylic acid | Additive | TM | A | B | C | D | TM |
| 5 | $K_2CO_3$ | $PdCl_2$ | $tBu_2PCy$ | $iPrCO_2H$ | — | 45.7 | 25.0 | 28.6 | 0.0 | 0.7 | 43.3 |
| 6 | $K_2CO_3$ | $PdCl_2$ | $tBu_2PCy$ | $iPrCO_2H$ | CuBr—$Me_2$ | 88.0 | 0.0 | 11.5 | 0.2 | 0.4 | 99.3 |

The abbreviations in the table are as follows.
—: not used
$tBu_2PCy$: di(tert-butyl)cyclohexylphosphine
$iPrCO_2H$: 2-methylpropanoic acid
CuBr—$SMe_2$: copper(I) bromide-dimethylsulfide complex As shown in the experimental number 1 to 4, the base, the palladium compound, the ligand, and the carboxylic acid are necessary elements for proceeding the reaction. Furthermore, the reaction proceeds without additives as shown in the experimental number 5 and 6; however, yield of target compound in the reaction was dramatically improved by adding additives.

Example 4

Synthesis of ethyl 2-(3-cyano-4-isobutoxyphenyl)-4-methylthiazole-5-carboxylate

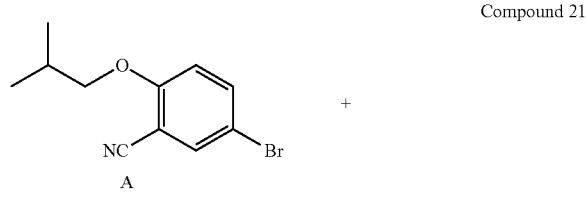

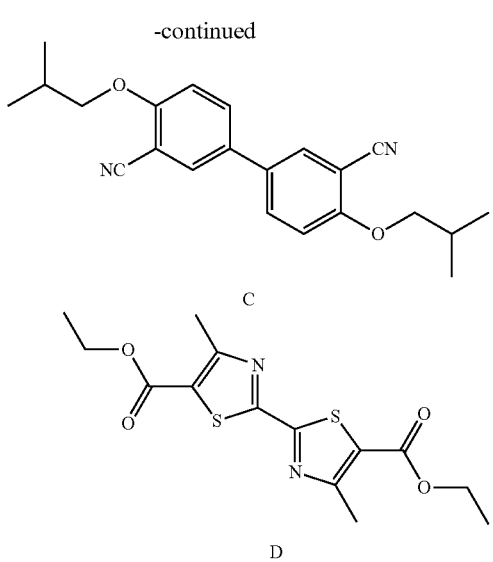

To a test tube-type reaction vessel (60 mL) were added ethyl 4-methylthiazole-5-carboxylate (2.14 g, 12.5 mmol), 5-bromo-2-isobutoxybenzonitrile (2.54 g, 10.0 mmol) obtained in the Reference Example 1, and a solvent (7.6 mL), a palladium compound (0.025 mmol), a ligand (0.10 mmol), a base (21.0 mmol), carboxylic acid (0.10 mmol), an additive (0.10 mmol), and a reducing agent (0.10 mmol) listed in the Table 10. Thereafter, the reaction vessel was filled with nitrogen gas and sealed air-tight and the mixed solution was heated to 140° C. and stirred for 24 hours. After the completion of the reaction, a portion of the reaction solution was diluted with xylene and DMSO and the resulting solution was analyzed by HPLC measurement. The total HPLC area % of the compound A to D and TM was adjusted to 100%, the calculated yield of the subject material was computed from each HPLC area %. Calculation of the calculated yield from the HPLC area % of subject material was carried out by applying corresponding numbers in the following calculation formula.

Yield (%) of TM=total amount of TM (mol)/[{total amount of A (mol)+total amount of C (mol)×2+ total amount of TM (mol)}]×100

Total amount of each compound (mol)=HPLC area value (mAU) of each compound/HPLC area value (mAU/mol) per mol of each compound The results are shown in Table 10. Note that the experimental number 22 in the Table 10 was performed by using n-butyl acetate as a solvent, causing the conversion of a part of ethyl esters in the compound TM, B, and D to butyl esters. Thus HPLC area % of the corresponding ethyl esters and butyl esters were added and presented.

TABLE 10

| Experimental No. | Reaction condition | | | | | | | HPLC area % | | | | | Calculated Yield (%) |
|---|---|---|---|---|---|---|---|---|---|---|---|---|---|
| | Solvent | Base | Palladium | Ligand | Carboxylic acid | Additive | Reducing agent | TM | A | B | C | D | TM |
| 7 | Xylene | $K_2CO_3$ | $PdCl_2$ | $PCy_3$—$HBF_4$ | $iPrCO_2H$ | CuBr—$SMe_2$ | — | 83.9 | 0.0 | 15.3 | 0.5 | 0.3 | 97.4 |
| 8 | Xylene | $K_2CO_3$ | $PdCl_2$ | $tBu_2PCy$ | 1-ad-$CO_2H$ | CuCl | — | 88.2 | 0.0 | 11.5 | 0.0 | 0.3 | 100.0 |
| 9 | Xylene | $K_2CO_3$ | $PdCl_2$ | $tBuPCy_2$ | PivOH | Cu(OAc) | — | 84.8 | 0.0 | 14.5 | 0.3 | 0.4 | 98.6 |
| 10 | Xylene | $K_2CO_3$ | $PdCl_2$ | $tBu_3P$—$HBF_4$ | 2-Me—$BuCO_2H$ | CuBr | — | 88.5 | 0.0 | 11.0 | 0.0 | 0.5 | 100.0 |
| 11 | Xylene | $K_2CO_3$ | $PdBr_2$ | $tBu_3P$—$HBF_4$ | $iPrCO_2H$ | CuBr | — | 87.3 | 0.0 | 11.7 | 0.0 | 1.0 | 100.0 |
| 12 | Xylene | $K_2CO_3$ | $PdBr_2$ | $tBu_2PCy$ | 1-ad-$CO_2H$ | CuCl | — | 87.8 | 0.0 | 11.7 | 0.0 | 0.5 | 100.0 |
| 13 | Xylene | $K_2CO_3$ | $PdBr_2$ | $tBuPCy_2$ | $iPrCO_2H$ | Cu(OAc) | — | 83.8 | 0.0 | 15.2 | 0.6 | 0.4 | 97.2 |
| 14 | Xylene | $K_2CO_3$ | $Pd(OPiv)_2$ | $tBu_2PCy$ | — | CuBr | — | 87.3 | 0.0 | 12.4 | 0.0 | 0.2 | 100.0 |
| 15 | Xylene | $K_2CO_3$ | $Pd(OPiv)_2$ | $tBu_2PCy$ | PivOH | CuBr | — | 88.6 | 0.0 | 11.0 | 0.0 | 0.4 | 100.0 |
| 16 | Xylene | $K_2CO_3$ | Crotyl Dimer | $tBu_2PCy$ | PivOH | CuBr | — | 87.9 | 0.0 | 11.6 | 0.0 | 0.5 | 100.0 |
| 17 | Xylene | $K_2CO_3$ | $Pd(dba)_2$ | $tBu_2PCy$ | $iPrCO_2H$ | CuBr | — | 87.8 | 0.0 | 11.9 | 0.0 | 0.3 | 100.0 |
| 18 | Xylene | $Na_2CO_3$ | $PdCl_2$ | $tBu_2PCy$ | $iPrCO_2H$ | CuBr | — | 87.5 | 0.0 | 11.3 | 0.1 | 1.1 | 99.3 |
| 19 | Xylene | $KHCO_3$ | $PdCl_2$ | $tBu_2PCy$ | $iPrCO_2H$ | CuBr | $Et_3SiH$ | 88.2 | 0.0 | 11.2 | 0.0 | 0.6 | 100.0 |
| 20 | Xylene | $K_2CO_3$ | $PdCl_2$ | $tBu_2PCy$ | $iPrCO_2H$ | CuBr | Zn | 86.2 | 0.0 | 13.3 | 0.1 | 0.4 | 99.4 |
| 21 | Xylene | $K_2CO_3$ | $PdCl_2$ | $tBu_2PCy$ | $iPrCO_2H$ | CuBr | — | 86.4 | 0.0 | 13.2 | 0.0 | 0.4 | 100.0 |
| 22 | n-Butyl acetate | $K_2CO_3$ | $PdCl_2$ | $tBu_2PCy$ | $iPrCO_2H$ | CuBr | — | 83.8 | 0.0 | 16.1 | 0.0 | 0.1 | 100.0 |
| 23 | Diglyme | $K_2CO_3$ | $PdCl_2$ | $tBu_2PCy$ | $iPrCO_2H$ | CuBr | — | 81.0 | 0.0 | 18.5 | 0.3 | 0.2 | 98.3 |
| 24 | Xylene | $K_2CO_3$ | $PdCl_2$ | $tBu_2PCy$ | $iPrCO_2H$ | AgCl | — | 86.6 | 0.0 | 13.0 | 0.0 | 0.5 | 100.0 |
| 25 | Xylene | $K_2CO_3$ | $PdCl_2$ | $tBu_2PCy$ | n-Hexadec. n-octadec·$CO_2H$ | CuBr | — | 86.7 | 0.0 | 12.1 | 0.0 | 1.3 | 100.0 |
| 26 | Xylene | $K_2CO_3$ | $PdCl_2$ | $tBu_2PCy$ | 3.5-diMe-1-ad-$CO_2H$ | CuBr | — | 88.5 | 0.0 | 11.5 | 0.0 | 0.0 | 100.0 |
| 27 | Xylene | $K_2CO_3$ | $PdCl_2$ | $Cy_2P(C_6H_4)$-1,3-dioxorane | $iPrCO_2H$ | CuBr | — | 87.3 | 0.0 | 12.7 | 0.0 | 0.0 | 100.0 |
| 28 | Xylene | $K_2CO_3$ | $PdCl_2$ | RuPhos | $iPrCO_2H$ | CuBr | — | 87.6 | 0.0 | 11.5 | 0.0 | 0.9 | 100.0 |
| 29 | Xylene | $K_2CO_3$ | $PdCl_2$ | XPhos | $iPrCO_2H$ | CuBr | — | 86.7 | 0.0 | 12.1 | 0.0 | 1.2 | 100.0 |
| 30 | Xylene | $K_2CO_3$ | $PdCl_2$ | SPhos | $iPrCO_2H$ | CuBr | — | 87.3 | 0.0 | 11.5 | 0.0 | 1.2 | 100.0 |
| 31 | Xylene | $K_2CO_3$ | $PdCl_2$ | $Cy_2P(CH_2)_4PCy_2$ | $iPrCO_2H$ | CuBr | — | 85.5 | 0.0 | 13.6 | 1.0 | 0.0 | 95.5 |

As shown in Table 10, the present invention can be conducted by using various solvents, bases, palladium compounds, ligands, carboxylic acids, and additives.

As shown in the experimental number 14, the reaction proceeds efficiently even when the carboxylic acid salt of the palladium compound is used instead of using the palladium compound and the carboxylic acid independently.

The abbreviations in Table 10 are as follows:
$PCy_3$-$HBF_4$: tricyclohexylphosphinetetrafluoroborate
$tBuPCy_2$: tert-butyldicyclohexylphosphine
1-ad-$CO_2H$: 1-adamantanecarboxylic acid
$tBu_3P$—$HBF_4$: tri-tert-butylphosphine tetrafluoroborate
PivOH: pivalic acid
Cu(OAc): copper(I) acetate
2-Me-$BuCO_2H$: 2-methylbutanoic acid
$Pd(OPiv)_2$: palladium(II) pivalate
Crotyl Dimer: crotyl palladium(II) chloride dimer
$Pd(dba)_2$: bis(dibenzylideneacetone) palladium(0)
$Et_3SiH$: triethylsilane
Diglyme: diethylene glycol dimethyl ether
n-Hexadec. n-octadec. $CO_2H$: 2-hexadecyloctadecanoic acid
3,5-diMe-1-ad-$CO_2H$: 3,5-dimethyl-1-adamantanecarboxylic acid
$Cy_2P(C_6H_4)$-1,3-dioxorane: 2-(2'-dicyclohexylphosphinophenyl)-1,3-dioxo lane
$Cy_2P(CH_2)_4PCy_2$: 1,4-bis(dicyclohexylphosphino)butane

[Industrial Applicability]

A novel coupling method comprising coupling between a phenyl derivative represented by formula (1) and a heterocyclic derivative represented by formula (2) in the presence of a palladium compound, a ligand capable of coordinating to the palladium compound, a base, and $C_1$ to $C_{40}$ carboxylic acid, furthermore one kind of additive or more to obtain a phenyl-substituted heterocyclic derivative represented by formula (3) of the present invention is useful to produce a xanthine oxidase inhibitor, which is a therapeutic agent for hyperuricemia, or intermediates thereof in a short process, with high yield and at low cost.

The invention claimed is:

1. A production method comprising reacting a compound represented by the following formula (1)

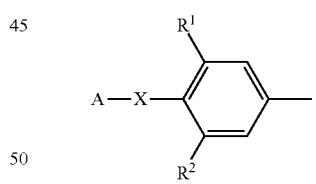

(wherein in formula (1),
$R^1$ represents a hydrogen atom or halogen atom;
$R^2$ represents a hydrogen atom, a cyano group, a nitro group, a halogen atom, a formyl group or a halomethyl group;
A represents a hydrogen atom, a $C_1$ to $C_8$ alkyl group, a $C_3$ to $C_6$ cycloalkyl group, a phenyl group, a fluorine atom (only when X is bond), or protecting group for a hydroxyl group (only when X is an oxygen atom),
A may be substituted with 1 to 3 substituents, such substituents include a group selected from the group consisting of a halogen atom, a $C_1$ to $C_4$ alkyl group, a $C_1$ to $C_4$ alkoxy group, a $C_1$ to $C_4$ alkylthio group, a $C_3$ to $C_6$ cycloalkyl group, a phenyl group, a phenoxy group, and a pyridyl group;

X represents a bond (only when A is a phenyl group or a fluorine atom), or an oxygen atom;
and Y represents a leaving group),
and a compound represented by the following formula (2)

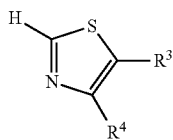

(2)

(wherein in formula (2),
H represents a hydrogen atom;
$R^3$ represents a —COOR$^{3a}$ or —COR$^{3b}$;
$R^{3a}$ represents a hydrogen atom, a $C_1$ to $C_4$ alkyl group, or an ester protecting group of a carboxyl group;
$R^{3b}$ represents an amide-type protecting group of a carboxyl group formed an amide with an adjacent carbonyl group; and
$R^4$ represents a hydrogen atom, a halogen atom, or $C_i$ to $C_4$ alkyl,
in the presence of
(i) a palladium compound,
(ii) a ligand capable of coordinating to the palladium compound or a salt thereof,
(iii) a base,
(iv) a $C_1$ to $C_{40}$ carboxylic acid or a salt thereof
(v) at least one additive selected from the group of consisting of copper, silver, and salts thereof, and complexes thereof;
to produce a phenyl-substituted heterocyclic derivative represented by the following formula (3)

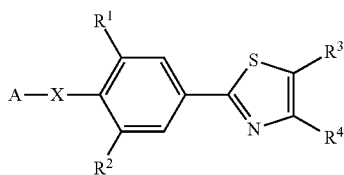

(3)

(Wherein in formula (3),
the definition of A, X, $R^1$ and $R^2$ is the same as defined in formula (1), and that of $R^3$ and $R^4$ is the same as in formula (2)).

2. The method of production according to claim 1, wherein A is a $C_1$ to $C_5$ alkyl group.

3. The method of production according to claim 1, wherein A is an isobutyl group.

4. The method of production according to claim 1, wherein X is an oxygen atom.

5. The method of production according to claim 1, wherein $R^1$ is a hydrogen atom.

6. The method of production according to claim 1, wherein $R^2$ is a cyano group.

7. The method of production according to claim 1, wherein Y represents a halogen atom, —OCO$_2$-($C_1$ to $C_4$ alkyl group), —OCO$_2$-(phenyl group), —OSO$_2$-($C_1$ to $C_4$ alkyl group), —OSO$_2$-(phenyl group), or a diazonium group, and ,in Y, the $C_1$ to $C_4$ alkyl group can be substituted with 1 to 3 halogen atoms, and the phenyl group can be substituted with 1 to 5 optional substituents selected from halogen atoms and $C_1$ to $C_4$ alkyl groups.

8. The method of production according to claim 1, wherein $R^3$ is COOR$^{3a}$ and $R^{3a}$ is a $C_1$ to $C_4$ alkyl group.

9. The method of production according to claim 1, wherein $R^4$ is a methyl group.

10. The method of production according to claim 1, wherein the palladium compound is zerovalent palladium, or a salt of monovalent or divalent palladium.

11. The method of production according to claim 1, wherein the palladium compound is palladium(II) acetate (Pd(OAc)$_2$), palladium(II) propionate (Pd(O(C=O)CH$_2$CH$_3$)$_2$), palladium(II) 2-methylpropanoate (Pd(O(C=O)CH(CH$_3$)$_2$)$_2$), palladium(II) pivalate (Pd(OPiv)$_2$), palladium(II) chloride (PdCl$_2$), palladium(II) bromide (PdBr$_2$), or palladium(0).

12. The method of production according to claim 1, wherein the palladium compound is palladium(II) 2-methylpropanoate (Pd(O(C=O)CH(CH$_3$)$_2$)$_2$), palladium(II) pivalate (Pd(OPiv)$_2$), palladium(II) chloride (PdCl$_2$), palladium(II) bromide (PdBr$_2$), or palladium(0).

13. The method of production according to claim 1, wherein the ligand is a phosphine-type ligand.

14. The method of production according to claim 13, wherein the phosphine-type ligand is a phosphine-type ligand represented by $R^5P(R^6)R^7$ ($R^5$ and $R^6$ are each independently a $C_3$ to $C_8$ alkyl group or an alicyclic hydrocarbon group wherein the number of hydrogen atoms bonded to each carbon atom of $R^5$ and $R^6$ which bind to a phosphorus atom is 0 or 1, $R^7$ is a $C_1$ to $C_8$ alkyl group, an alicyclic hydrocarbon group, a $C_6$ to $C_{12}$ aryl group, or a heteroaryl group).

15. The method of production according to claim 14, wherein the phosphine-type ligand is tri(tert-butyl)phosphine, di(tert-butyl)methylphosphine, tert-butyldicyclohexylphosphine, di(tert-butyl)cyclohexylphosphine, or tri(cyclohexyl)phosphine.

16. The method of production according to claim 1, wherein the base is a hydroxide of an alkali metal or a Group 2 element, a fluoride of an alkali metal, a phosphate of an alkali metal, or a carbonate or a hydrogen carbonate of an alkali metal or a Group 2 element.

17. The method of production according to claim 16, wherein the base is potassium carbonate, potassium hydrogen carbonate, sodium carbonate, or sodium hydrogen carbonate.

18. The method of production according to claim 1, wherein the carbon atom of the carboxyl group at the α-position in the $C_1$ to $C_{40}$ carboxylic acid is not the carbon atom on the aromatic ring and the number of hydrogen atoms bonded to the carbon atom of the carboxyl group at the α-position is 0 or 1.

19. The method of production according to claim 18, wherein the $C_1$ to $C_{40}$ carboxylic acid contains one carboxyl group and consists of only carbon atoms and hydrogen atoms as constituent atoms except for the carboxyl group.

20. The method of production according to claim 19, wherein the $C_1$ to $C_{40}$ carboxylic acid is 2-methylpropanoic acid or pivalic acid.

21. The method of production according to claim 1, wherein a divalent palladium salt of the $C_1$ to $C_{40}$ carboxylic acid is used instead of using (i) the palladium compound and (iv) the $C_1$ to $C_{40}$ carboxylic acid and a salt thereof independently.

22. The method of production according to claim 1, wherein a monovalent copper salt or a monovalent silver salt of the $C_1$ to $C_{40}$ carboxylic acid is used instead of using (iv) the $C_1$ to $C_{40}$ carboxylic acid or a salt thereof and (v) the additive independently.

23. The method of production according to claim 1, wherein the additive is zerovalent copper or a salt of monovalent copper.

24. The method of production according to claim 1, wherein the additive is at least one additive selected from the group consisting of copper(I) oxide, copper(I) fluoride, copper(I) chloride, copper(I) bromide, copper(I) iodide, copper (I) formate, copper(I) acetate, copper(I)propionate, copper(I) 2-methylpropanoate, copper(I) 2-ethylbutanoate, copper(I) 2-methylbutanoate, copper(I) 2-methylpentanoate, copper(I) 2-methylhexanoate, copper(I) 2-methylheptanoate, copper(I) 2,2-dimethylbutanoate, copper(I) 2,3-dimethylbutanoate, copper(I) 2,2-dimethylpentanoate, copper(I) 2,3,3-trimethylbutanoate, copper(I) 2-ethylhexanoate, copper(I) 2,2-diethylbutanoate, copper(I) 2,2,4-trimethylpentanoate, copper(I) 2-methyloctanoate, copper(I) 2-methylundecanoate, copper (I) 2-methylnonanoate, copper(I) pivalate, copper(I) cyclopropanoate, copper(I) 2,2,3,3-tetramethylcyclopropanoate, copper(I) cyclopentanoate, and copper(I) 1-adamantanecarboxylate.

25. The method of production according to claim 1, wherein the additive is zerovalent silver or a salt of monovalent silver.

26. The method of production according to claim 1, wherein the additive is at least one additive selected from the group consisting of silver(I) oxide, silver(I) fluoride, silver(I) chloride, silver(I) bromide, silver(I) iodide, silver(I) formate, silver (I) acetate, silver(I) propionate, silver(I) 2-methylpropanoate, silver(I) 2-ethylbutanoate, silver(I) 2-methylbutanoate, silver(I) 2-methylpentanoate, silver(I) 2-methylhexanoate, silver(I) 2-methylheptanoate, silver(I) 2,2-dimethylbutanoate, silver(I) 2,3-dimethylbutanoate, silver(I) 2,2-dimethylpentanoate, silver(I) 2,3,3-trimethylbutanoate, silver(I) 2-ethylhexanoate, silver(I) 2,2-diethylbutanoate, silver(I) 2,2,4-trimethylpentanoate, silver(I) 2-methyloctanoate, silver(I) 2-methylundecanoate, silver(I) 2-methylnonanoate, silver(I) pivalate, silver(I) cyclopropanoate, silver (I) 2,2,3,3-tetramethylcyclopropanoate, silver(I) cyclopentanoate, and silver(I) 1-adamantanecarboxylate.

* * * * *